United States Patent
Scheffold et al.

(10) Patent No.: US 10,513,687 B2
(45) Date of Patent: *Dec. 24, 2019

(54) METHOD FOR POLYCLONAL STIMULATION OF T CELLS BY FLEXIBLE NANOMATRICES

(71) Applicant: Miltenyi Biotec GmbH, Bergisch-Gladbach (DE)

(72) Inventors: Alexander Scheffold, Joachim Friedrich (DE); Mario Assenmacher, Bergisch-Gladbach (DE)

(73) Assignee: Miltenyi Biotec GmbH, Bergisch-Gladbach (DE)

( * ) Notice: Subject to any disclaimer, the term of this patent is extended or adjusted under 35 U.S.C. 154(b) by 162 days.

This patent is subject to a terminal disclaimer.

(21) Appl. No.: 14/035,809

(22) Filed: Sep. 24, 2013

(65) Prior Publication Data

US 2014/0087462 A1 Mar. 27, 2014

(30) Foreign Application Priority Data

Sep. 25, 2012 (EP) .................................. 12185939

(51) Int. Cl.
| | | |
|---|---|---|
| C12N 5/00 | (2006.01) | |
| C12N 5/02 | (2006.01) | |
| C12N 5/0783 | (2010.01) | |
| A61K 35/17 | (2015.01) | |

(52) U.S. Cl.
CPC ............ *C12N 5/0637* (2013.01); *A61K 35/17* (2013.01); *C12N 5/0075* (2013.01); *C12N 5/0636* (2013.01); *C12N 2501/51* (2013.01); *C12N 2501/515* (2013.01); *C12N 2501/998* (2013.01); *C12N 2533/70* (2013.01); *C12N 2539/00* (2013.01)

(58) Field of Classification Search
None
See application file for complete search history.

(56) References Cited

U.S. PATENT DOCUMENTS

| | | | | |
|---|---|---|---|---|
| 5,658,741 A | * | 8/1997 | Bolton .............. | A61K 47/48561 435/5 |
| 5,872,222 A | * | 2/1999 | Chang .................. | A61K 9/1271 530/388.75 |
| 6,117,982 A | | 9/2000 | Chang | |
| 8,012,750 B2 | | 9/2011 | Har-Noy | |
| 9,790,467 B2 | | 10/2017 | Kevlahan et al. | |
| 2002/0119568 A1 | * | 8/2002 | Berenson ............ | A61L 27/3804 435/446 |
| 2007/0086996 A1 | | 4/2007 | Har-Noy | |
| 2008/0317724 A1 | | 12/2008 | Kam et al. | |
| 2009/0291498 A1 | | 11/2009 | Har-Noy | |
| 2010/0151031 A1 | | 6/2010 | DeSimone et al. | |
| 2010/0284965 A1 | | 11/2010 | Fahmy et al. | |
| 2012/0121649 A1 | | 5/2012 | Santamaria | |

FOREIGN PATENT DOCUMENTS

| | | | | |
|---|---|---|---|---|
| EP | 1 257 632 B1 | 9/2007 | | |
| WO | WO-9412196 A1 | * 6/1994 | ............... | B82Y 5/00 |
| WO | WO-94/29436 A1 | 12/1994 | | |
| WO | WO-2009/072003 A2 | 6/2009 | | |
| WO | WO 2009117616 A2 | * 9/2009 | ......... | A61K 38/1709 |

OTHER PUBLICATIONS

Lijima et al.,1995, J. CHem. Phys. vol. 104: 2089-2092.*
Teo et al., 2003, Encyc. Nanosci and Nanotech., pp. 1-22.*
Choi et al., 2010, Ultrasound Med. biol. vol. 36: 58-67.*
Baroja, M.L. et al. (Apr. 15, 1989). "The Anti-T Cell Monoclonal Antibody 9.3 (Anti-CD28) Provides a Helper Signal and Bypasses the Need for Accessory Cells in T Cell Activation with Immobilized Anti-CD3 and Mitogen," *Cell Immunol.* 120(1):205-217.
Demento, S. et al. (Sep. 2009). "Biomimetic Approaches to Modulating the T Cell Immune Response With Nano- and Micro-Particles," 31st *Annual International Conference of the IEEE EMBS*, Minneapolis, MN, Sep. 2-6, 2009, pp. 1161-1166.
Dinauer, N. et al. (2005). "Selective Targeting of Antibody-conjugated Nanoparticles to Leukemic Cells and Primary T-Lymphocytes," *Biomaterials* 26:5898-5906.
Fahmy, T.M. et al. (2007). "Dendrimer-Based Nanomedicine. A Nanoscopic Multivalent Antigen—presenting Carrier for Sensitive Detection and Drug Delivery to T Cells," *Nanomedicine: Nanotechnology, Biology and Medicine* 3:75-85.

(Continued)

*Primary Examiner* — Amy E Juedes
(74) *Attorney, Agent, or Firm* — Morrison & Foerster LLP

(57) ABSTRACT

The present invention provides a method polyclonal stimulation of T cells, the method comprising contacting a population of T cells with a nanomatrix, the nanomatrix comprising a) a flexible matrix, wherein said matrix is of polymeric material; and b) attached to said polymeric flexible matrix one or more polyclonal stimulatory agents which provide activation signals to the T cells; thereby activating and inducing the T cells to proliferate; wherein the nanomatrix is 1 to 500 nm in size. At least one first and one second stimulatory agents are attached to the same or to separate flexible matrices. If the stimulatory agents are attached to separate beads, fine-tuning of nanomatrices for the stimulation of the T cells is possible.

12 Claims, 15 Drawing Sheets

(56) References Cited

OTHER PUBLICATIONS

Mescher, M.F. et al. (Oct. 1, 1992). "Surface Contact Requirements for Activation of Cytotoxic T Lymphocytes," *The Journal of Immunology* 149(7):2402-2405.
Steenblock, E.R. et al. (Apr. 2008). "A Comprehensive Platform for *Ex Vivo* T-cell Expansion Based on Biodegradable Polymeric Artificial Antigen-presenting Cells," *Molecular Therapy* 16(4):765-772.
International Search Report dated Dec. 20, 2013, for PCT Application No. PCT/EP2013/069854,filed on Sep. 24, 2013, 5 pages.
Written Opinion dated Dec. 20, 2013, for PCT Application No. PCT/EP2013/069854,filed on Sep. 24, 2013, 6 pages.

* cited by examiner

Transduction efficiency
(% CD8+MART-1tet+ among CD8+ cells)

| | αCD3+αCD28 | MACSiBeads | Nanomatrix | Soluble aCD3 |
|---|---|---|---|---|
| $T_N$ | 90.2 (84.4 - 98) | 45.9 (28.6 - 65.7) | 58.5 (35.6 - 80.3) | --- |
| $T_{CM}$ | 91.7 (86 - 96.4) | 86 (74.6 - 94.6) | 81.7 (63.1 - 91.3) | --- |
| $T_{EM}$ | 85.3 (69.7 - 91.8) | 82.5 (76.4 - 90.5) | 90.2 (68.8 - 95.1) | --- |
| PBMC | --- | --- | --- | 82.2 (72.8 - 91.8) |

FIG 7

METHOD FOR POLYCLONAL STIMULATION OF T CELLS BY FLEXIBLE NANOMATRICES

CROSS-REFERENCE TO RELATED APPLICATION

This application claims priority to European Application No. EP12185939, filed Sep. 25, 2012, incorporated herein by reference in its entirety.

FIELD OF INVENTION

The present invention relates generally to the field of immunology, in particular to processes for polyclonal stimulation of T cells by nanomatrices.

BACKGROUND OF THE INVENTION

Antibodies against CD3 are a central element in many T cell proliferation protocols. Immobilized on a surface, anti-CD3 delivers an activating and proliferation-inducing signal by crosslinking of the T cell receptor complex on the surface of T cells. By immobilizing anti-CD3 and anti-CD28 to simultaneously deliver a signal and a co-stimulatory signal, proliferation can be increased (Baroja et al (1989), Cellular Immunology, 120: 205-217). In WO09429436A1 solid phase surfaces such as culture dishes and beads are used to immobilize the anti-CD3 and anti-CD28 antibodies. Regularly, the immobilization on beads is performed on Dyna-Beads® M-450 having a size of 4.5 µm in diameter.

EP01257632B1 describes a method for stimulating a population of T-cells by simultaneous T-cell concentration and cell surface moiety ligation that comprises providing a population of cells wherein at least a portion thereof comprises T-cells, contacting the population of cells with a surface, wherein the surface has attached thereto one or more agents that ligate a cell surface moiety of at least a portion of the T-cell and stimulates at least that portion of T cells or a subpopulation thereof and applying a force that predominantly drives T-cell concentration and T-cell surface moiety ligation, thereby inducing T-cell stimulation. The term force as used herein refers to a force used to drive the cells and may include a variety of forces that function similarly, and include a force greater than gravitational force, a hydraulic force, a filtration force generated by transmembrane pressure, a centrifugal force, or a magnetic force. EP1257632B1 describes that ratios of particles to cells can vary, however certain preferred values include at least 1:4 to 6:1, with one preferred ratio being at least 2:1 beads per T-cell. Regularly, DynaBeads® M-450 having a size of 4.5 µm in diameter coupled to anti-CD3 and anti-CD28 antibodies were used in experiments in a bead/T-cell ratio of 3:1. Again, these methods use solid phase surfaces to co-immobilize T cell stimulation agents such as anti-CD3 and anti-CD28 antibodies. These surfaces are cell-sized and comparable with the T cells themselves.

US2008/0317724A1 discloses that the spatial presentation of signal molecules can dramatically affect the response of T cells to those signal molecules. For example, when anti-CD3 and anti-CD28 antibodies are placed on separate predefined regions of a substrate, T cells incubated on the substrate secrete different amounts of interleukin-2 and/or exhibit spikes in calcium, depending not only on the types but also on the spacing of these signal molecules. For example, a pattern was generated with anti-CD3 and anti-CD28 antibodies, where anti-CD3 antibodies occupied a central feature surrounded by satellite features of anti-CD28 antibodies that were spaced about 1 to 2 microns from the central anti-CD3 feature. When the anti-CD28 antibody features were spaced about 1 to 2 microns apart, the T cell secretion of interleukin-2 (IL-2) was enhanced compared to when the anti-CD3 and anti-CD28 antibodies were presented together to the T cells in "co-localized" features.

The publication of Erin R Steenblock and Tarek M Fahmy (Molecular Therapy vol. 16 no. 4, 765-772 April 2008) uses solid-surface nanoparticles (130 nm) and show that these nanoparticle stimulate T cells weaker than microparticles (8 µm). The authors stated that these findings are supported by those of previous reports (Mescher, M F (1992). J Immunol 149: 2402-2405.), demonstrating that micron-sized particles, which are close in size to T cells, provide optimal T-cell stimulation. Mesher's study demonstrated the critical importance of a large, continuous surface contact area for effective CTL activation. Using class I alloantigen immobilized on latex microspheres, particle sizes of 4 to 5 microns were found to provide an optimum stimulus. Below 4 microns, responses decreased rapidly with decreasing particle size, and large numbers of small particles could not compensate for suboptimal size.

U.S. Pat. No. 8,012,750B2 discloses a biodegradable device for activating T-cells. The biodegradable support is first formulated into a shape, such as a microsphere. The biodegradable supports then coated with a first material providing a reactive surface which is capable of binding to second materials. The second materials have a reactive surface which permits binding to surface structures on a cell. The biodegradable support can be formulated into various shapes. Microspheres are a preferred formulation because of the simplicity of manufacture and the spherical shape allows an increased surface area for interaction with cellular receptors. According to U.S. Pat. No. 8,012,750B2 nanospheres do not provide enough cross-linking to activate naive T-cells and thus can only be used with previously activated T-cells. Again, experimental data were generated with spheres co-immobilized with anti-CD3 and anti-CD28 antibodies ranging in size from 4 to 24 microns with a mean of 7 microns.

Taken together, beads or microspheres used in the state of the art for T cell activation via immobilized T cell stimulatory antibodies are cell-sized (mostly 1 to 10 µm in size), uniformly round-shaped particles. Beads of this size have several disadvantages with regard to their potential to interact with T cells as well as their production, handling and safety in clinical T cell therapy procedures.

1. Due to the solid surface of the bead the size of interaction area between the bead and cells is limited.
2. Their preparation is complex and costly as compared to soluble antibodies and it is especially inconvenient to generate them in cGMP quality, e.g. due to their size no sterile filtration is possible, sedimentation complicates handling, i.e. constant particle number/volume during filling and antibody loading.
3. They are inconvenient to use for in vitro processes to generate T cell therapeutics for in vivo use,
   since they have to be added to cells in defined cell/bead ratios at defined density cell/beads per surface area,
   adaption of stimulation strength is only possible to some extent, since the T cell stimulation strength is mostly determined by the density of antibodies on the cell surface and not by the number of beads/cell
   aliquoting is inaccurate due to sedimentation,
   sterile filtration is not possible
   due to their size they might affect cell viability and function and they cannot simply be removed from cells by centrifugation. Therefore either special protocols for "bead removal" or biodegradable particles have been developed. However both methods suffer from inaccuracies with regard to the actual number of residual beads after the removal process, leaving behind a certain risk for toxic effects if T cell stimulatory beads are injected into patients. This problem is particularly relevant because of the size of the particles, since each single particle on its own might still have retained the capacity to activate T cells in vivo.

Therefore, there is a need for an improved in-vitro method for T cell stimulation.

All references cited herein, including patent applications and publications, are incorporated by reference in their entirety.

SUMMARY OF THE INVENTION

Surprisingly, it was found that polyclonal T cell stimulatory agents such as antibodies, e.g. against CD3 and CD28, attached to nanomatrices, which are characterised by a flexible polymeric matrix backbone (non-solid surface), which may have embedded within the matrix additional functional compounds, such as magnetic nanocrystalls, can be used to stimulate naïve and memory T cells in vitro, although their diameter is smaller than 1 µm, preferentially smaller than 500 nm, more preferentially smaller than 200 nm. Contrary thereto, it was found that beads with solid surfaces of the same size as the nanomatrices used herein are not able to stimulate T cells at all or to a similar level like the nanomatrices which is in accordance with the well established opinion of the person skilled in the art. Due to their small size the nanomatrices per se, without antibodies attached thereto, do not alter structure, function, activity status or viability of cells, i.e. they do not cause perturbance in the cells and do not interfere with subsequent analyses, experiments and therapeutic applications of the stimulated cells. In addition, preferentially, the nanomatrix is biodegradable and non-toxic to living cells, i.e. the nanomatrix is a biologically inert entity with regard to alterations of the cell function. Therefore the nanomatrix used in the method of the present invention improves the in-vitro stimulation of T-cells by saving the viability of the cells.

In addition surprisingly, it was found that the polyclonal T cell stimulatory agents such as antibodies, e.g. against CD3 and CD28, attached to nanomatrices may be conjugated to separate nanomatrices (instead of conjugating to the same nanomatrix), which can be mixed hereafter for optimised use. In general, the ratio of nanomatrices to cells is larger than 100:1, preferentially larger than 500:1, most preferentially larger than 1000:1. This results in the possibility of fine-tuning of the nanomatrices used for stimulation of the target T cells, e.g. it facilitates the production process and quality control of the single nanomatrices and improves the flexibility of the reagent, e.g. facilitating the optimisation of the activation conditions for specialised T cell subsets by titrating various CD3 and CD28 concentrations and ratios.

In general, the present invention provides the use of the nanomatrices disclosed herein for the in-vitro stimulation of T cells.

The present invention provides a method for polyclonal stimulation of T cells, the method comprising contacting a population of T cells with a nanomatrix, wherein the nanomatrix comprises a flexible matrix, and has attached thereto one or more agents which provide activation signals to the T cells; thereby activating and inducing the T cells to proliferate; and wherein the nanomatrix is 1 to 500 nm, preferentially 10 to 200 nm, in size. Preferentially, the nanomatrix is biologically inert with regard to alterations of the cell function. In addition preferentially, the nanomatrix is biodegradable.

The stimulated and optionally expanded T cells achieved with the present invention can be used in subsequent therapeutic or non-therapeutic applications without the need for eliminating or removing the nanomatrix due to the property of the nanomatrix of being biologically inert with regard to alterations of the cell function Alternatively, due to being soluble or colloidal the nanomatrices can easily be diluted by repeated washing steps to effective concentrations below the T cell activation threshold after the T-cell stimulation process.

The nanomatrix is 1 to 500 nm, preferentially 10 to 200 nm in size. The nanomatrix is a flexible matrix consisting of a polymeric material but has no solid phase surface in contrast to beads or microspheres. Agents such as anti-CD3 and/or anti-CD28 antibodies which allow for polyclonal stimulation of T cells are attached to the flexible matrix. Within the matrix additional substances, such as magnetic nanocrystalls, fluorescent dyes, etc., can be embedded and add additional functions to the nanomatrix without altering its basic flexible structure, surface features, or cell interaction parameters of the nanomatrix.

Figure 5A:
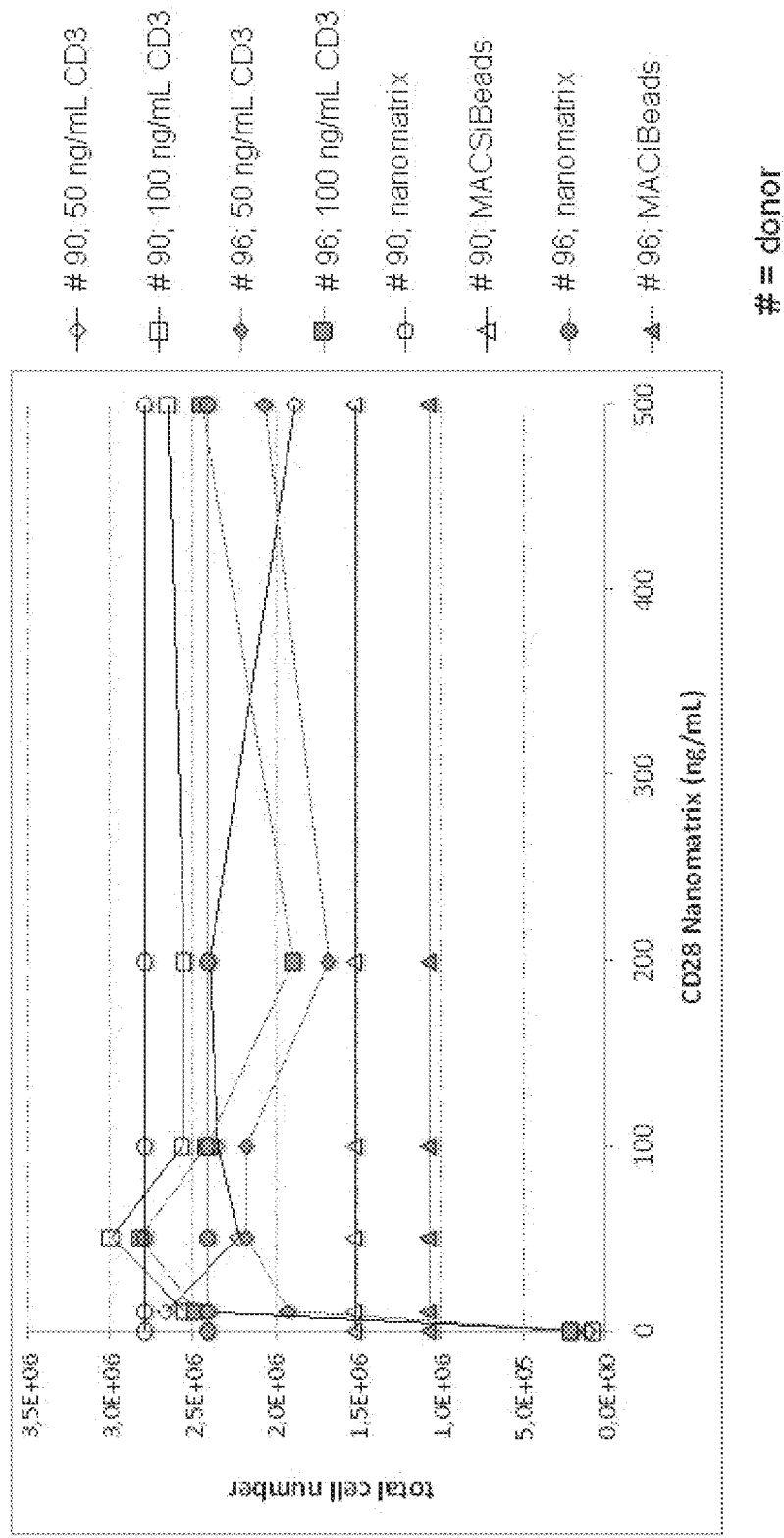
Figure 5B:
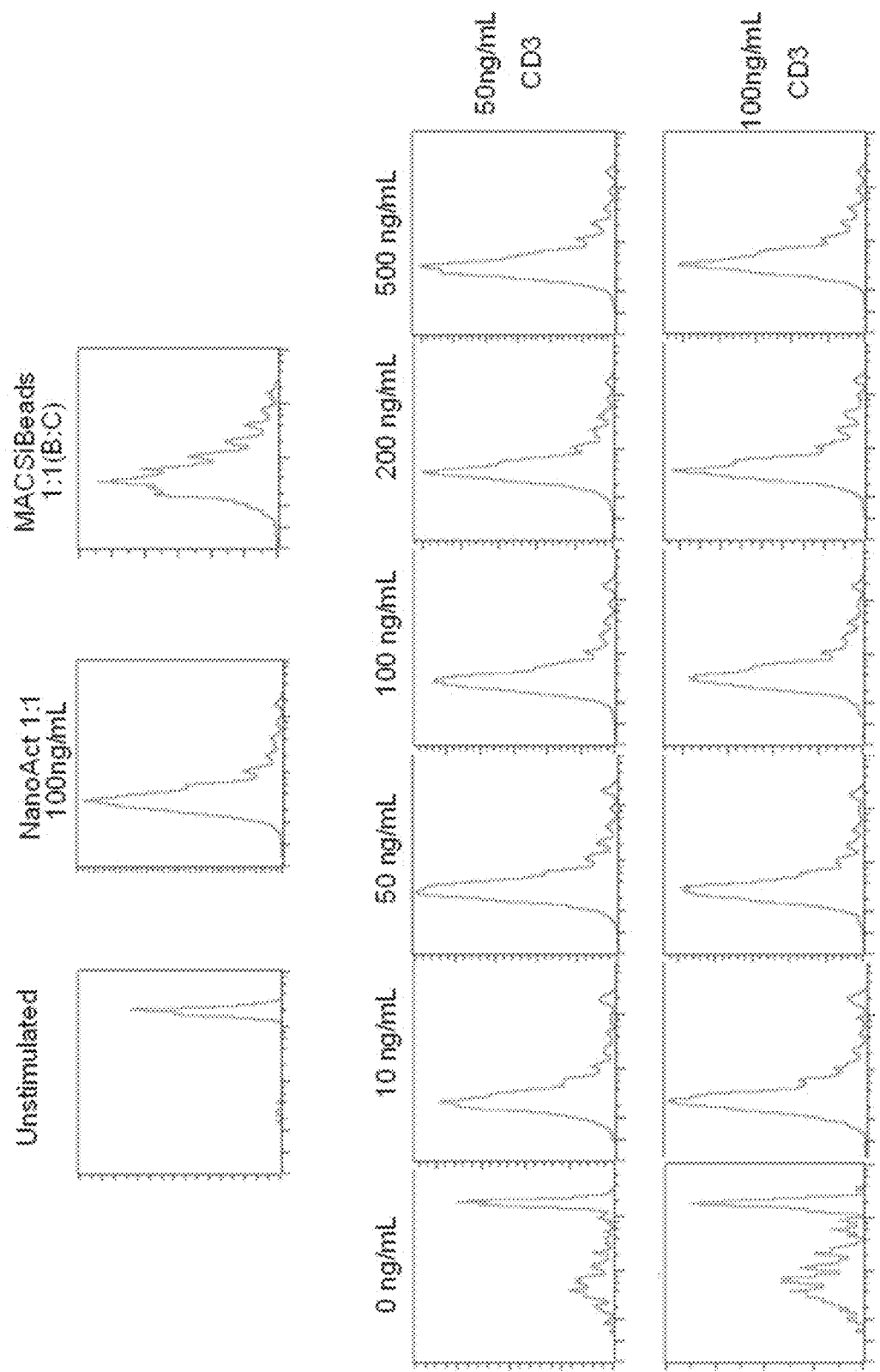

FIGS. 5A and 5B show comparison of CD3 and CD28 conjugated to different nanomatrices versus conjugated to the same nanomatrix. Sorted human naive CD4 and CD8 T cells were stimulated either with CD3/CD28 conjugated nanomatrices or CD3 and CD28 conjugated to different nanomatrices at the indicated concentrations (effective CD3 concentration) in the presence of IL-2 for 7 days. As a high control CD3/CD28 conjugated MACSiBeads were used. The absolute number of viable cells in the culture at day 7 is given (A). Results from two donors are depicted. In addition the cells were labelled with CFSE and the proliferative activity measured on day 5 after activation (1 representative donor).

Figure 6A:
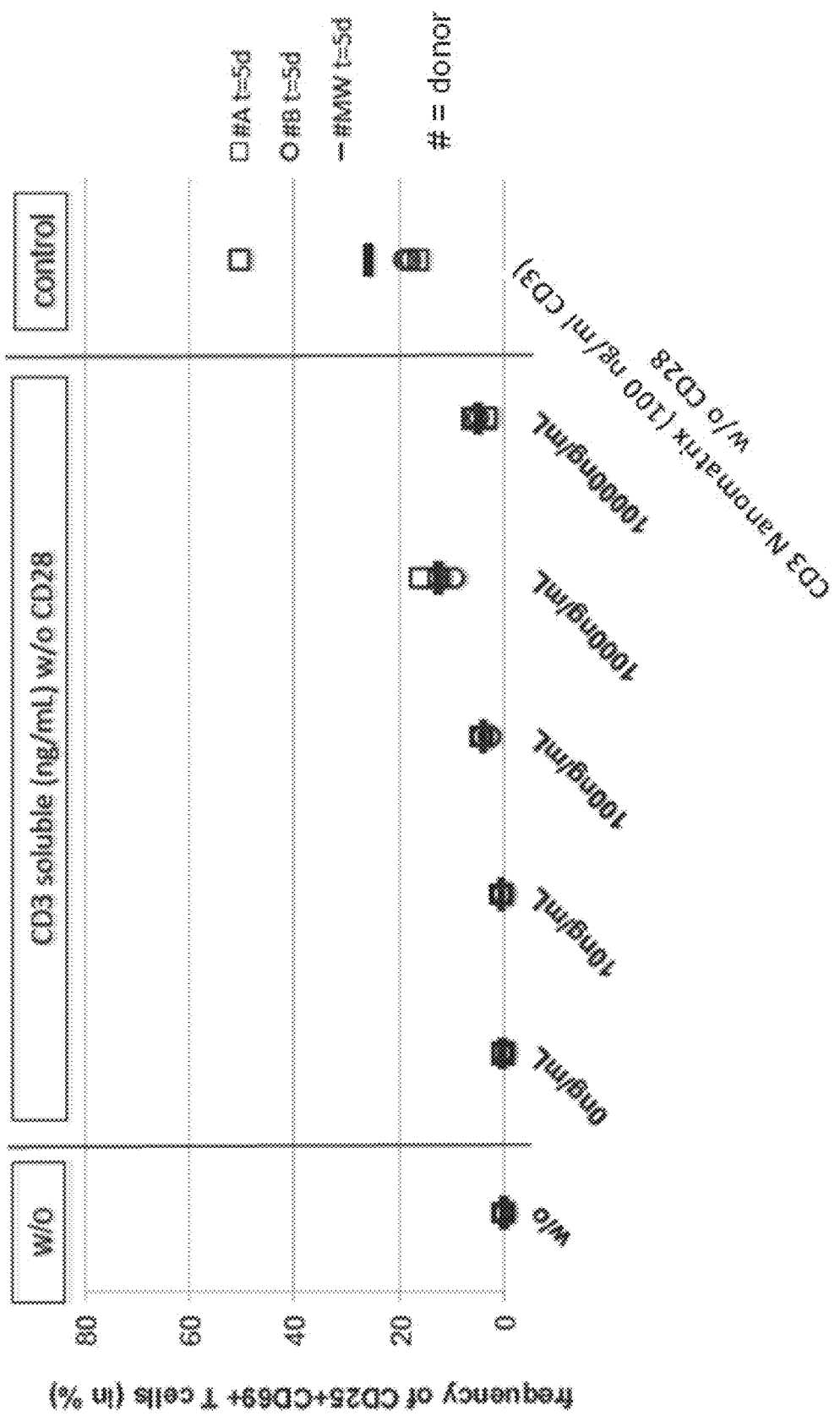
Figure 6B:
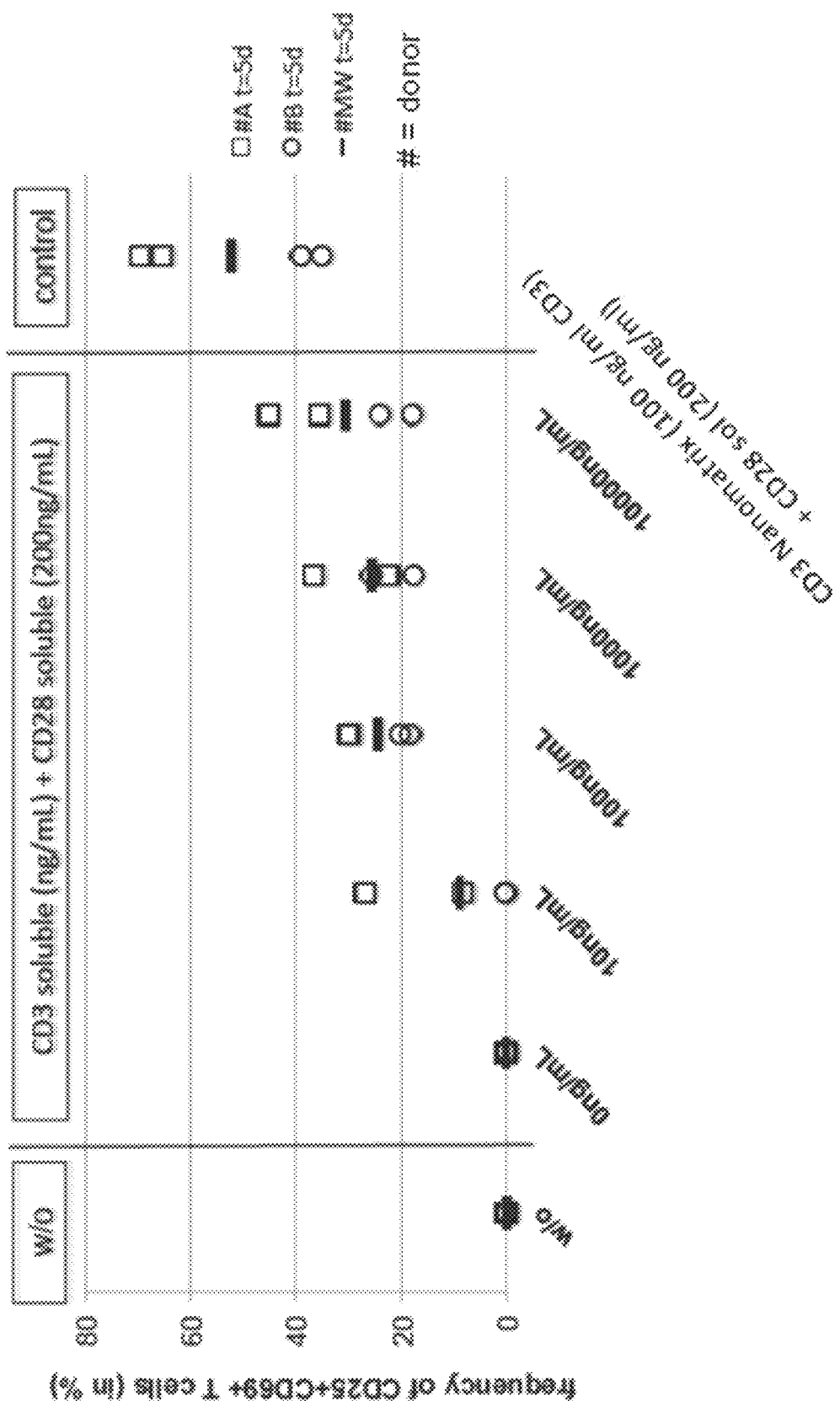
Figure 6C:
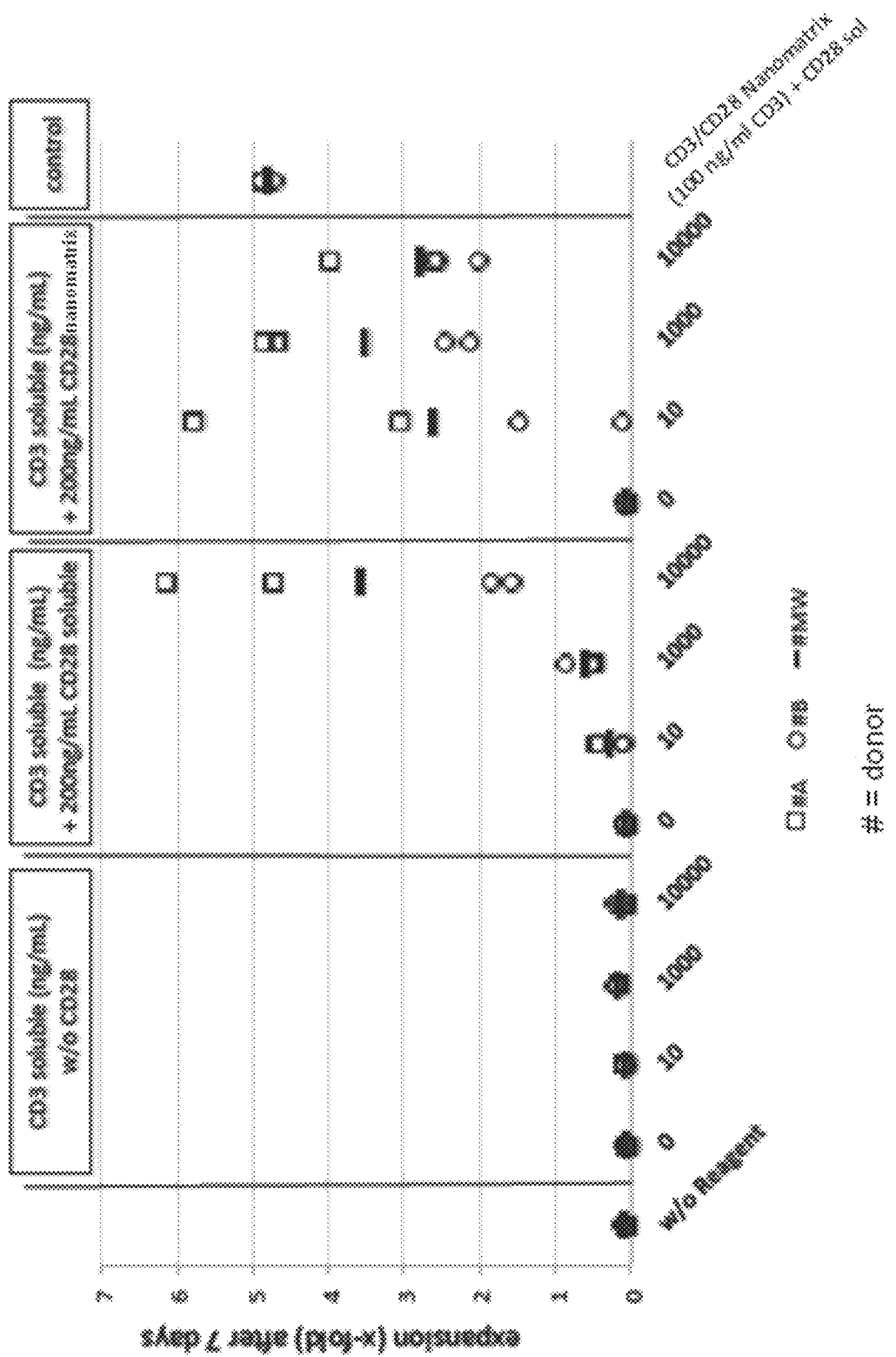

FIG. 6A, FIG. 6B and FIG. 6C show a comparison of soluble CD3 or CD28 antibodies to CD3 or CD28 antibodies conjugated to nanomatrices. Naive CD4 and CD8 T cells were isolated and stimulated in vitro in the presence of IL-2 using soluble CD3 (0-10000 ng/mL) w/o CD28 (FIG. 6A) or in the presence of soluble CD28 (200 ng/ml) (FIG. 6B) and compared to CD28 conjugated to nanomatrix (200 ng/ml) and analysed for early activation markers CD25/CD69 on day 5 or for expansion (FIG. 6C) on day 7. 2 donors were analysed in duplicates.

FIG. 7 shows transduction efficiency of isolated T cell subsets stimulated with various stimulation agents. T cell subsets, naïve ($T_N$, CD62L+CD45RA+), central memory ($T_{CM}$, CD62L+CD45RA-) and effector ($T_{EM}$, CD62L-CD45RA-) T cells activated using CD3/CD28 nanomatrices, plate-bound CD3+ soluble CD28 or CD3/CD28 conjugated MACSibeads and transduced them using a retroviral vector expressing a TCR specific for MART-1. As a standard total PBMC were activated using soluble CD3/CD28. The frequency of transduced cells expressing the MART-1 TCR was determined using a fluorescently labelled MART-1/HLA-A2 tetramer.

Figure 8:
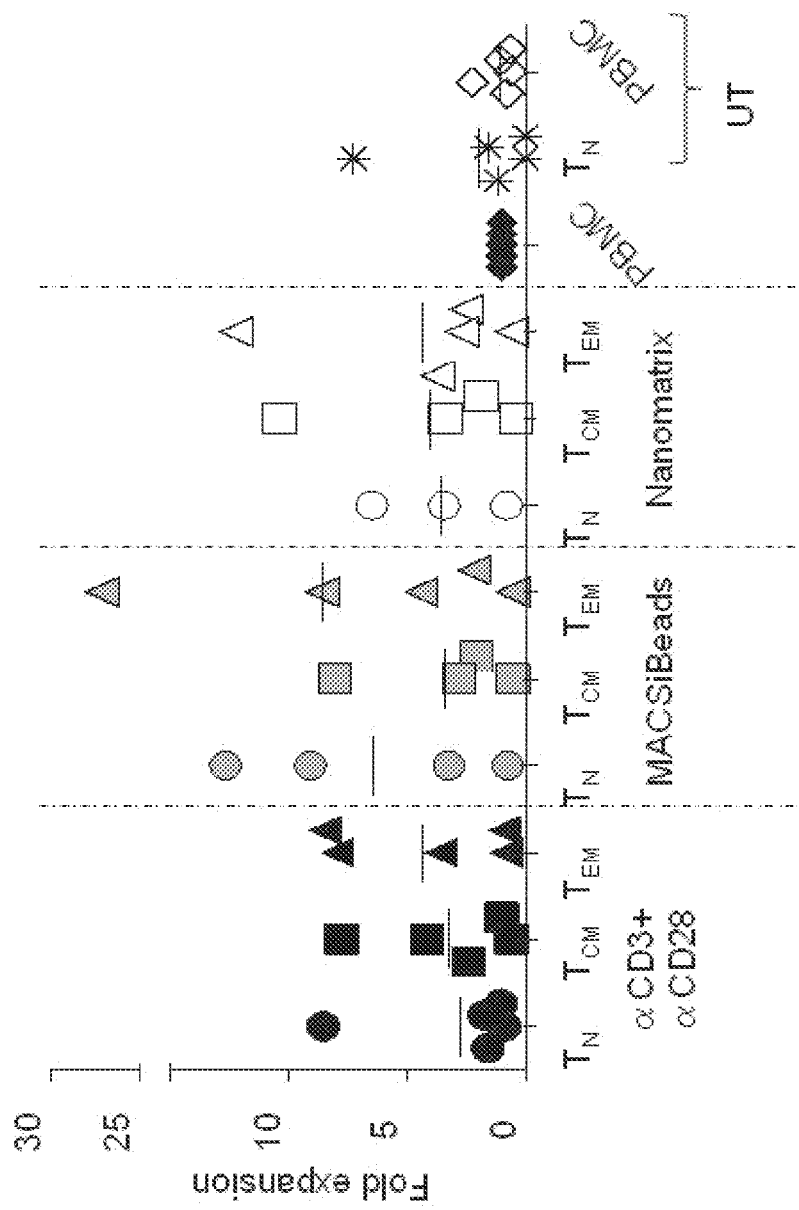

FIG. 8 shows enriched T cell subsets expand at least like PBMC or better. $CD8^+$ T cell subsets from freshly isolated PBMC from melanoma patients were isolated and the stimulated with coated CD3 plus soluble CD28 (CD3+CD28 in the graph) or with CD3/CD28/CD2 coated MACSiBeads (MACSiBeads in the graph) or with CD3/CD28 Nanomatrix in the presence of IL2. After 2 days of stimulation cells have been transduced to express MART-1 TCR. In the graph is reported the fold expansion of each culture at day 13-15 after stimulation. The fold expansion values are relative to soluble CD3 stimulated PBMC that shows a fold expansion of 57.61±17.75

Figure 9:
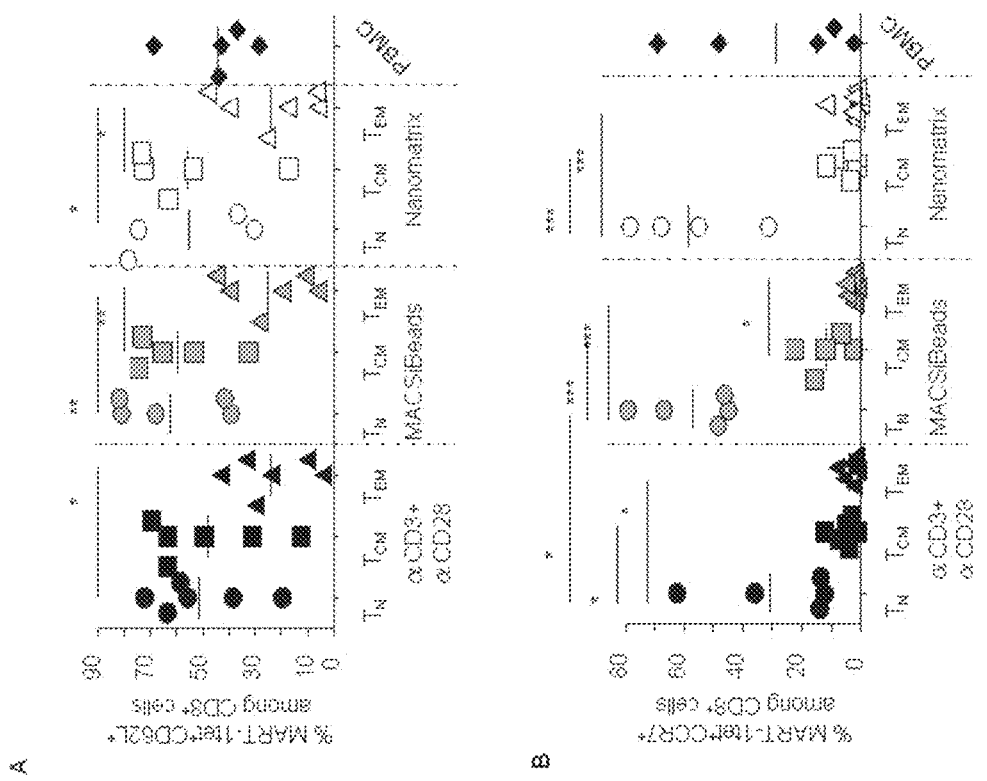

FIG. 9 shows naïve and central memory cells stimulated with MACSiBeads or CD3/CD28 nanomatrix show a less terminal differentiated phenotype. PBMC were freshly isolated from leukapheresis of melanoma patients. CD8+ T cell subsets were enriched and then stimulated with CD3+CD28 or MACSiBeads or CD3/CD28 nanomatrix in the presence of IL2. PBMC instead were stimulated with soluble CD3 and IL2. Cells were transduced to express MARt-1 TCR 48 h after stimulation. The data here were obtained 13-15 days after stimulation of each culture. Frequencies of A) MART-1 tetramer$^+$ CD62L$^+$ and B) MART-1 tetramer$^+$CCR7$^+$ cells among CD8$^+$ T cells are shown. After IL2 withdrawal cells were stained for CD127, CD57 and CD27 markers or stimulated with MART-1$^+$ HLA-A2$^+$ melanoma cell line in the presence of CD107a antibody and Monensin for 5 h. Statistical analysis of C) MART-1 tetramer$^+$ CD127$^+$; D) MART-1 tetramer$^+$ CD27$^+$; E) MART-1 tetramer$^+$ CD57$^+$ and F) CD107a$^+$ cells among CD8$^+$ T cells frequencies.

Figure 10:
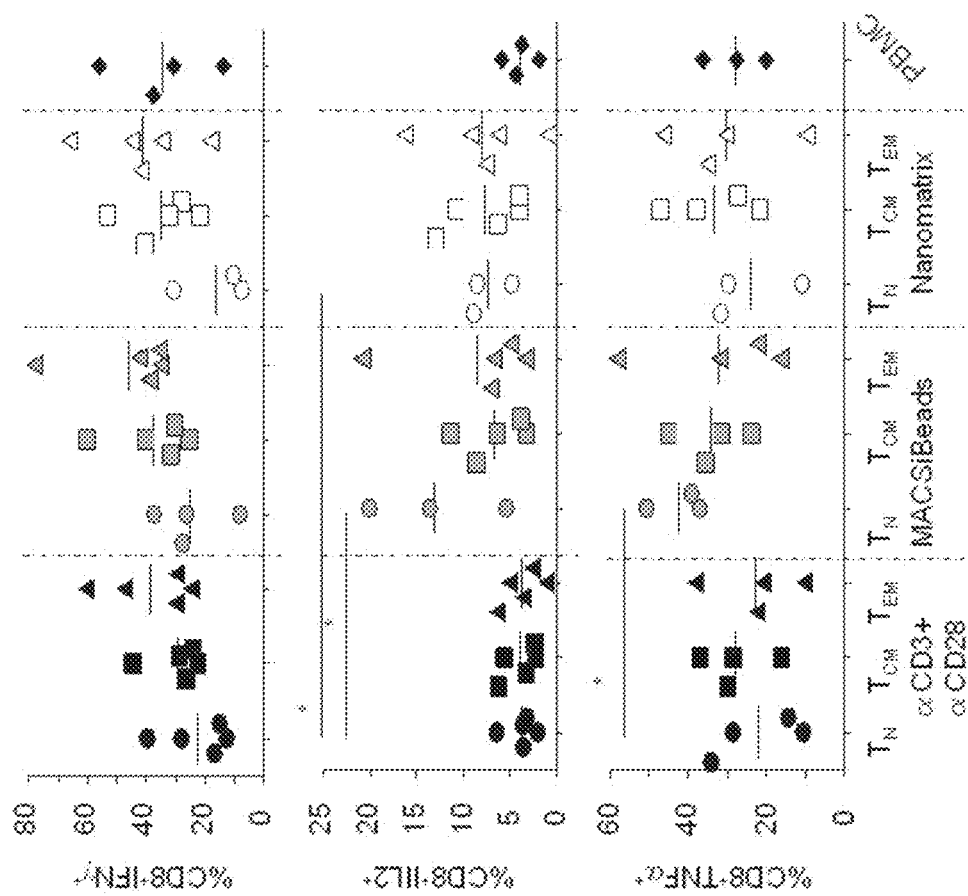

FIG. 10 shows cytokine secretion upon MART-1 restimulation in CD8$^+$ T cell subsets. CD8$^+$ T cell subsets from freshly isolated PBMC from melanoma patients were isolated and the stimulated with CD3+CD28 MACSiBeads or with CD3/CD28 nanomatrix in the presence of IL2. PBMC from the same melanoma patient were stimulated with soluble CD3 and IL2. After 2 days of stimulation cells have been transduced to express MART-1 TCR and cultured for a total 13-15 days. Afterwards cells were washed out from IL2 and rested for further 2 days and then restimulated with MART-1$^+$ HLA-A2$^+$ melanoma cell line for 6 h. The cytokine production was determined by intracellular staining. Graphs show the frequencies of A) IFNγ$^+$; B) IL2$^+$ and C) TNFα$^+$ CD8+ T cells.

DETAILED DESCRIPTION OF THE INVENTION

It was a well established opinion in the scientific community that particles smaller than 1 μm are not convenient to stimulate T cells effectively because such small particles do not provide enough cross-linking to activate T cells. Therefore, generally, beads or microspheres with solid phase surfaces used to stimulate T cells are always larger than 1 μm in size in the state of the art, regularly they are cell-sized.

Now unexpectedly, the inventors found that nanomatrices being smaller than 1 μm, preferentially smaller than 500 nm, more preferentially smaller than 200 nm, having a flexible matrix and having attached thereto polyclonal stimulatory agent(s) are convenient to stimulate T cells. It is essential to the present invention that the nanomatrix being smaller than 500 nm has no solid phase surface in contrast to beads or microspheres of the same size (see Example 3). The nanomatrix is like a mesh or net consisting of a polymeric material, preferentially dextran. The nanomatrix is very plastic resulting in the ability to snuggle to the cell surface membrane of target cells, i.e. the T cells which shall be activated. Therefore, the nanomatrix binds with its agents attached to the flexible matrix to the respective receptors (antigens) on the cell surface, whereby the flexibility of the matrix allows optimal interaction with the binding partners. To a certain degree the shape of the nanomatrix adapts to the target cell surface thereby extending the contacting surface between nanomatrix and target cell. Due to the size of the nanomatrix of 1 to 500 nm, preferentially 10 to 200 nm, they are too small to cause perturbance in the cell, i.e. the nanomatrix is biologically inert with regard to alterations of the cell function. Such perturbances triggered by direct cell/bead contact is problematic if beads or microspheres of 1 μm or larger in size are used. In addition, preferentially, the nanomatrix is biodegradable and non-toxic to the cells due to the composition consisting of biodegradable polymeric material such as a polymer of dextran. In consequence, the nanomatrix is a completely biologically inert entity with regard to alterations of the cell function but biodegradable. Therefore there is no need to remove the nanomatrix after contacting it with the T cells for stimulation and proliferation. No disturbing effects occur due to the presence of the nanomatrices in an activated T cell composition for subsequent analysis, experiments and/or clinical applications of these cells.

In addition, due to being soluble or colloidal the unbound nanomatrices can easily be diluted by repeated washing steps to effective concentrations below the T cell activation threshold after the T-cell stimulation process.

The flexible matrix of the nanomatrix has attached thereto one or more polyclonal stimulatory agents which provide activation signal(s) to the T cells, thereby activating and inducing the T cells to proliferate. The agents are molecules which are capable of binding to a cell surface structure and induce the polyclonal stimulation of the T cells. One example for agents attached to the flexible matrix of the nanomatrix is anti-CD3 monoclonal antibody (mAb) in combination with a co-stimulatory protein such as anti-CD28 mAb. Other examples are anti-CD2, anti-CD137, anti-CD134, Notch-ligands, e.g. Delta-like1/4, Jagged1/2 either alone or in various combinations with anti-CD3. T cells to be stimulated are e.g. naïve T cells, memory T cells, CD4 Treg and CD8 Treg cells. Preferentially, the polyclonal stimulatory agent attached to the flexible matrix of the nanomatrix is anti-CD3 monoclonal antibody (mAb) in combination with the co-stimulatory protein anti-CD28 mAb.

Therefore, in one aspect the present invention provides a method for polyclonal stimulation of T cells, the method comprising contacting a population of T cells with a nanomatrix, the nanomatrix comprising a) a flexible matrix, wherein said matrix is of polymeric material; and b) attached to said polymeric flexible matrix one or more polyclonal stimulatory agents which provide activation signals to the T cells; thereby activating and inducing the T cells to proliferate;

and wherein the nanomatrix is 1 to 500 nm, preferentially 10 to 200 nm, in size.

The nanomatrix may be biologically inert with regard to alteration of the cell function.

In addition, or alternatively, the nanomatrix may be biodegradable.

The nanomatrix may be of cGMP quality for clinical applications. Sterility can be achieved e.g. by sterile filtration using filters with suitable pore size (200 nm) or by other methods well known by the person skilled in the art.

The contacting can occur e.g. in vitro in any container capable of holding cells, preferably in a sterile environment. Such containers may be e.g. culture flasks, culture bags, bioreactors or any device that can be used to grow cells (e.g. the sample processing system of WO2009072003).

The nanomatrix used in the present invention can be a nanomatrix wherein at least one first agent and one second agent are attached to the same flexible matrix. Nanomatrices of this kind are contacted with T cells, thereby activating and inducing the T cells to proliferate. The ratio of the first and the second agent attached to the same flexible matrix may be in the range of the ratios of 100:1 to 1:100, preferentially between 10:1 and 1:10, most preferentially between 2:1 and 1:2.

In addition surprisingly, it was found that the nanomatrix of the present invention also can be a nanomatrix wherein at least one first agent and one second agent are attached to separate flexible matrices. A mixture of these nanomatrices is contacted with T cells, thereby activating and inducing the T cells to proliferate (see Example 6). The ratio and/or concentration of the flexible matrix having attached thereto the first agent and the flexible matrix having attached thereto the second agent may vary to yield optimal stimulation results depending on the kind of T cells used and/or agents used. This facilitates the optimisation of the activation conditions for specialised T cell subsets by titrating various concentrations and ratios of the flexible matrix having attached thereto the first agent and the flexible matrix having attached thereto the second agent. It is advantageous that generally the ratio of nanomatrices to cells is larger than 100:1, preferentially larger than 500:1, most preferentially larger than 1000:1. The large amount of nanomatrices per cell allows for a fine-tuning of the separate labelled nanomatrices which would be impossible with lower ratios of 1:10 to 10:1 commonly used by stimulation of T cells using cell-sized beads.

The nanomatrix used in the present invention is a nanomatrix wherein the flexible matrix consists of a polymeric, preferentially biodegradable material which is non-toxic to cells. Preferentially, the nanomatrix used in the present invention is a nanomatrix wherein the flexible matrix consists of a polymer of dextran.

The nanomatrix used in the present invention can be a nanomatrix wherein the flexible matrix is the only or at least main component of the nanomatrix regardless the agents which are attached thereto. But the nanomatrix used in the present invention also can be a nanomatrix wherein the nanomatrix carries magnetic, paramagnetic, superparamagnetic nano-crystals, or fluorescent dyes embedded into the flexible matrix, preferentially embedded into the polymer of dextran.

The nanomatrix used in the present invention can be used in a method for stimulating T-cells with this nanomatrix wherein the nanomatrix is not removed in subsequent applications of the stimulated T cells.

Alternatively, the nanomatrix used in the present invention also can be used in a method for stimulating T-cells with this nanomatrix wherein the nanomatrix is removed before subsequent applications of the stimulated T cells.

In another aspect the present invention also provides a composition comprising i) the nanomatrix, the nanomatrix comprising
  a) a flexible matrix, wherein said matrix is of polymeric material; and
  b) attached to said polymeric flexible matrix one or more agents which provide activation signals to the T cells; thereby activating and inducing the T cells to proliferate;

and wherein the nanomatrix is 1 to 500 nm, preferentially 10 to 200 nm, in size ii) a population of T cells which are activated and induced to proliferate triggered by the contact between said nanomatrix and cells.

The nanomatrix may be biologically inert with regard to alteration of the cell function.

The nanomatrix may be biodegradable.

Agents are attached to the same or separate nanomatrices at high density, with more than 25 µg per mg nanomatrix, preferentially with more than 50 µg per mg nanomatrix.

This composition may be convenient for generating T cell therapeutics for in vivo use (pharmaceutical composition). The composition also can be used in other subsequent analyses and experiments.

In another aspect the present invention also provides a composition or a pharmaceutical composition comprising a population of stimulated and (optionally expanded) T cells produced according to the method of the present invention. The pharmaceutical composition may comprise a population of stimulated T cells produced by the method of the present invention, wherein the method is performed in a closed cell culture system such as the sample processing system of WO2009072003.

Nanomatrices can be prepared by various methods known in the art, including solvent evaporation, phase separation, spray-drying, or solvent extraction at low temperature. The process selected should be simple, reproducible and scalable. The resulting nanomatrices should be free-flowing and not aggregate in order to produce a uniform syringeable suspension. The nanomatrix should also be sterile. This can be ensured by e.g. filtration, a terminal sterilization step and/or through aseptic processing. A preparation of nanomatrices is described in Example 1.

Definitions

The term "flexible matrix" as used herein refers to a flexible matrix consisting of a polymeric, preferentially biodegradable material which is non-toxic to cells. The flexible matrix is the only or at least main component of the nanomatrix regardless the agents which are attached thereto.

The flexible matrix may be of collagen, purified proteins, purified peptides, polysaccharides, glycosaminoglycans, or extracellular matrix compositions. A polysaccharide may include for example, cellulose, agarose, dextran, chitosan, hyaluronic acid, or alginate. Other polymers may include polyesters, polyethers, polyanhydrides, polyalkylcyanoacrylates, polyacrylamides, polyorthoesters, polyphosphazenes, polyvinylacetates, block copolymers, polypropylene, polytetrafluorethylene (PTFE), or polyurethanes. The polymer may be lactic acid or a copolymer. A copolymer may comprise lactic acid and glycolic acid (PLGA). Preferentially the flexible matrix is a polymer of dextran.

The flexible matrix defines the property of the nanomatrix of being very plastic leading to the ability to snuggle to the cell surface membrane of target cells, i.e. the T cells which shall be activated and proliferated. Therefore, the nanomatrix tightly binds with its agents attached to the flexible matrix to the cells because the flexibility of the matrix provides optimal access of the attached ligands or antibodies to their cell surface receptors or antigens. Due to this property the nanomatrix has the ability to provide enough cross-linking to activate T cells regardless of the small size of the structure, i.e. smaller than 1 μm, preferentially smaller than 500 nm, more preferentially smaller than 200 nm, in size. The adaptability of the nanomatrix caused by the flexible nanostructure extends the contacting area between cell surface membrane and the nanomatrix resulting in more efficient bindings between cell surface molecules and agents attached to the flexible matrix.

In some embodiments the flexible matrix may embed magnetic, paramagnetic or superparamagnetic nano-crystalls or other substances which add additional functional properties such as fluorescent dyes without altering the basic flexible structure and/or surface features, i.e. interaction with target cells.

The term "agent" which is attached to the flexible matrix of the nanomatrix as used herein refers to molecules which are capable of binding to a cell surface structure and contribute to a polyclonal stimulation of the T cells. Examples of suitable agents for use in the present invention include agents such as synthesized compounds, nucleic acids and proteins, including polyclonal or monoclonal antibodies, and fragments or derivatives thereof, and bioengineered proteins, such as fusion proteins. In one example, the agents are mitogenic proteins. Mitogenic proteins are two or more proteins that are able to deliver the requisite minimum of two signals to T-cells in order to cause the T-cells to become activated. Examples of mitogenic proteins are anti-CD3 and anti-CD2 monoclonal antibodies (mAb) in combination with a co-stimulatory protein such as and including proteins specific for one or more of the following T-cell surface molecules: CD28, CD5, CD4, CD8, MHCI, MHCII, CTLA-4, ICOS, PD-1, OX40, CD27L (CD70), 4-1BBL, CD30L and LIGHT, including the corresponding ligands to these surface structures, or fragments thereof.

Other suitable agents include agents capable of delivering a signal to T-cells through cytokine receptors such as IL-2R, IL-12R, IL-1R, IL-15R; IFN-gammaR, TNF-alphaR, IL-4R, and IL-10R, including monoclonal antibodies (mAbs) to these receptors, fusion proteins with a reactive end specific for these receptors and the corresponding ligands to these receptors or fractions thereof. Other suitable agents include any agent capable of binding to cellular adhesion molecules on T-cells such as mAbs, fusion proteins and the corresponding ligands or fractions thereof to adhesion molecules in the following categories: cadherins, ICAM, integrins, and selectins. Examples of adhesion molecules on T-cells are: CD44, CD31, CD18/CD11a (LFA-1), CD29, CD54 (ICAM-1), CD62L (L-selectin), and CD29/CD49d (VLA-4). Other suitable agents include any agents capable of binding to chemokine receptors, including those in the C—C and C—X—C categories. Examples of chemokine receptors associated with T-cell function include CCR1, CCR2, CCR3, CCR4, CCR5, and CXCR3.

An agent may be attached or coupled to the flexible matrix by a variety of methods known and available in the art. The attachment may be covalent or noncovalent, electrostatic, or hydrophobic and may be accomplished by a variety of attachment means, including for example, chemical, mechanical, enzymatic, or other means whereby a agent is capable of stimulating the cells. For example, the antibody to a cell surface structure first may be attached to the matrix, or avidin or streptavidin may be attached to the matrix for binding to a biotinylated agent. The antibody to the cell surface structure may be attached to the matrix directly or indirectly, e.g. via an anti-isotype antibody. Another example includes using protein A or protein G, or other non-specific antibody binding molecules, attached to matrices to bind an antibody. Alternatively, the agent may be attached to the matrix by chemical means, such as cross-linking to the matrix.

As used herein, the term "antibody" is intended to include polyclonal and monoclonal antibodies, chimeric antibodies, haptens and antibody fragments, and molecules which are antibody equivalents in that they specifically bind to an epitope on the antigen. The term "antibody" includes polyclonal and monoclonal antibodies of any isotype (IgA, IgG, IgE, IgD, IgM), or an antigen-binding portion thereof, including, but not limited to, F(ab) and Fv fragments such as sc Fv, single chain antibodies, chimeric antibodies, humanized antibodies, and a Fab expression library.

The term "biologically inert" as used herein refers to the properties of the nanomatrix, that it is non-toxic to living cells and does not induce strong alterations of the cell function via physical interaction with the cell surface, due to its small size, except the specific ligand/receptor triggering function of the attached ligands or antibodies. The nanomatrices, in addition, may be biodegradable, e.g. degraded by enzymatic activity or cleared by phagocytic cells. The biodegradable material can be derived from natural or synthetic materials that degrade in biological fluids, e.g. cell culture media and blood. The degradation may occur using enzymatic means or may occur without enzymatic means. The biodegradable material degrades within days, weeks or few months, which may depend on the environmental conditions it is exposed to. The biodegradable material should be non-toxic and non-antigenic for living cells and in humans. The degradation products must produce non-toxic by-products.

An important aspect in the context of being biologically inert is the fact that the nanomatrix does not induce strong alteration in structure, function, activity status or viability of labelled cells, i.e. it does not cause perturbance of the cells and does not interfere with subsequent experiments and therapeutic applications of the stimulated cells. The mechanical or chemical irritation of the cell is decreased due to the properties of the nanomatrix of being very small, i.e. nano-scale range, and having a flexible matrix which rather snuggles to the cell surface than altering the shape of the cell surface or exerting strong shearing force to the cells, e.g. resulting in membrane rupture.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

EMBODIMENTS

In one embodiment of the present invention a first nanomatrix of 1 to 500 nm, preferentially 10 to 200 nm in size consists of a flexible matrix of a polymer of dextran and has attached thereto one agent, e.g. anti CD3 mAb. A second nanomatrix of 1 to 500 nm, preferentially 10 to 200 nm in size consists of a flexible matrix of a polymer of dextran and has attached thereto another agent, e.g. anti CD28 mAb. In this case the nanomatrix of the present invention is a nanomatrix wherein at least one first agent and one second agent are attached to separate flexible matrices.

A mixture of these nanomatrices is contacted with T cells, thereby activating and inducing the T cells to proliferate.

Fine-tuning of nanomatrices for the stimulation of the T cells is easily performed due to the high ratio of nanomatrices to cells (normally larger than 500:1).

In another embodiment of the present invention a nanomatrix of 1 to 500 nm, preferentially 10 to 200 nm in size consists of a flexible matrix of a polymer of dextran and has attached thereto one agent, e.g. anti CD3 mAb. In this case the nanomatrix of the present invention is a nanomatrix wherein at least one first agent is attached to flexible matrices. This nanomatrix is contacted with T cells, thereby activating and inducing the T cells to proliferate.

A second or more (multiple) co-stimulating agents, e.g. anti CD28 mAb, may be added as soluble agents to optimize or support the activation induced by the nanomatrix with the first agent attached thereto.

In another embodiment of the present invention a nanomatrix of 1 to 500 nm, preferentially 10 to 200 nm in size consists of a flexible matrix of a polymer of dextran and has attached thereto two agents which provide activation signals to the cell, e.g. anti CD3 mAb and anti CD28 mAb. In this case the nanomatrix of the present invention is a nanomatrix wherein at least one first agent and one second agent are attached to the same flexible matrix.

Nanomatrices of this kind are contacted with T cells, thereby activating and inducing the T cells to proliferate.

In another embodiment of the present invention a nanomatrix of 1 to 500 nm, preferentially 10 to 200 nm in size consists of a flexible matrix of a polymer of dextran and has attached thereto multiple agents which provide activation signals to the cell, e.g. anti-CD3 mAb and anti-CD28 mAb, anti ICOS, anti-CD137 or other known co-stimulatory molecules. In this case the nanomatrix of the present invention is a nanomatrix wherein at least one first agent and multiple other agents are attached to the same flexible matrix.

Nanomatrices of this kind are contacted with T cells, thereby activating and inducing the T cells to proliferate.

In another embodiment of the present invention a nanomatrix of 1 to 500 nm, preferentially 10 to 200 nm in size consists of a flexible matrix of a polymer of dextran and has attached thereto one or more agents which provide activation signals to the cells, e.g. anti CD3 mAb and/or anti CD28 mAb. In addition the nanomatrix carries magnetic, paramagnetic or superparamagnetic nano-crystals, embedded into the polymer.

The nanomatrix is contacted with T cells, thereby activating and inducing the T cells to proliferate. Optionally, after stimulating of T cells the unbound magnetic, paramagnetic or superparamagnetic nanomatrix may be removed by applying a magnetic field gradient. Alternatively, the cells labelled with the magnetic nanomatrices may be separated by applying a magnetic field gradient, in particular a high-gradient magnetic field, and subsequent expansion of the purified T cells.

Although there is no need to remove the nanomatrix after activation and proliferation of the population of T cells due to their property of being biologically inert with regard to alteration one might optionally remove the nanomatrix with mild washing conditions, which are sufficient to wash way the nanomatrices from the cells or cell culture. The nanomatrices can easily be diluted by repeated washing steps to effective concentrations below the T cell activation threshold. This optionally removing step is much easier performed with the nanomatrices than with beads or microspheres well known in the state of the art due to their small size. If the nanomatrix carries magnetic, paramagnetic or superparamagnetic nano-crystals, embedded into the polymer than optionally the removal step can be performed by applying a magnetic field gradient to the cell/nanomatrix mixture.

The method of the invention can be used to expand selected T cell populations for use in treating an infectious disease or cancer. The resulting T cell population can be genetically transduced and used for immunotherapy or can be used for in vitro analysis of infectious agents such as HIV. Proliferation of a population of CD4+ cells obtained from an individual or patient, e.g. infected with HIV, can be achieved and the cells rendered resistant, e.g. to HIV infection. Following expansion of the T cell population to sufficient numbers, the expanded T cells are re-infused into the individual or patient. Similarly, a population of tumor-infiltrating lymphocytes can be obtained from an individual afflicted with cancer and the T cells stimulated to proliferate to sufficient numbers and restored to the individual. In addition, supernatants from cultures of T cells expanded in accordance with the method of the invention are a rich source of cytokines and can be used to sustain T cells in vivo or ex vivo.

In another embodiment of the present invention a nanomatrix as described in any proceeding embodiment may be used in a closed cell culture system, e.g. the sample processing system of WO2009072003. The nanomatrices have optimal connectivity to such a closed cell culture system, they can be easily sterile filtrated and integrated into the closed cell culture system. They ease the processes of the closed cell culture system, i.e. stimulation of the T cells or other target cells) because no removal of the nanomatrices after the stimulation (and expanding) process is necessary as described herein.

The use of the method of the present invention within a closed cell culture system such as the sample processing system of WO2009072003 results in a safe and easy way to produce a pharmaceutical composition of stimulated T cells due to the reduced risk of e.g. contaminating agents such as other eukaryotic cells, bacteria or viruses (safer and faster handling by the operator).

The present invention has broad applicability to any cell type having a cell surface moiety that may be stimulated. In this regard, many cell signaling events can be enhanced by the method of the present invention. Such methodologies can be used therapeutically in an ex vivo setting to activate and stimulate cells for infusion into a patient or could be used in vivo, to induce cell signaling events on a target cell population. Preferentially the target cells of the method are T cells, but are in no way limited thereto.

Prior to stimulation of T cells by the present invention the T cells may be directly identified and/or separated or isolated from blood, peripheral mononuclear blood cells (PBMC), body tissue or cells from tissue fluids. The cells are normally identified and/or separated from cell samples from mammals such as humans, mouse, or rat, but especially from humans and preferably from test subject and/or patients. The separation is performed by well known sorting methods in the art. This includes for example affinity chromatography or any other antibody-dependent separation technique known in the art. Any ligand-dependent separation technique known in the art may be used in conjunction with both positive and negative separation techniques that rely on the physical properties of the cells. An especially potent sorting technology is magnetic cell sorting. Methods to separate cells magnetically are commercially available e.g. from Invitrogen, Stemcell Technologies, Cellpro, Advanced Magnetics, or Miltenyi Biotec. In addition to mixtures of T cells with other cells, such as monocytes, macrophages, dendritic cells, B cells or other cells which are part of hematologic cell samples, such as blood or leukapheresis, highly purified T cell populations can be used for contacting with the presented invention, including T cell subpopulations, such as CD4+ T cells, CD8+ T cells, NKT cells, γ/δ T cells, α/β T cells, CD4+CD25+Foxp3+ regulatory T cells, naïve T cells (CD45RA+CCR7+ and/or CD62L+) or central memory T cells (CD45R0+CCR7+), effector memory T cells (CD45R0+CCR7−) or terminal effector T cells (CD45RA+ CCR7−). Nanomatrices provide sufficient crosslinking activity to the T cell receptor, therefore additional crosslinking, e.g. via Fc-receptor expressing cells such as monocytes or dendritic cells is not required for activation.

Target cell populations, such as the T cell populations obtained via the present disclosure may be administered either alone, or as a pharmaceutical composition in combination with diluents and/or with other components such as IL-2 or other cytokines or cell populations. Briefly, pharmaceutical compositions of the present disclosure may comprise a target cell population as described herein, in combination with one or more pharmaceutically or physiologically acceptable carriers, diluents or excipients. A pharmaceutical composition may comprise a) a population of T cells, wherein said T cells are proliferated to therapeutically effective amounts according to the present invention; and b) one or more pharmaceutically or physiologically acceptable carriers, diluents or excipients. Such a composition may contain traces of nanomatrices which are biologically inert with regard to alteration of the cell function but may be biodegradable and which are non-toxic and non-antigenic to humans.

Compositions of the present disclosure are preferably formulated for intravenous administration.

Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

EXAMPLES

Example 1: Preparation of Nanomatrices

Magnetic nanomatrices were produced by a modification of the procedure of Molday and MacKenzie. Ten grams of Dextran T40 (Pharmacia Uppsala, Sweden), 1.5 g $FeCl_3$ 6 $H_2O$ and 0.64 g $FeCl_2$ 4 $H_2O$ are dissolved in 20 ml $H_2O$, and heated to 40° C. While stirring, 10 ml 4N NaOH are added slowly and the solution is heated to 70° C. for 5 min. The particle suspension is neutralized with acetic acid. To remove aggregates the suspension is centrifuged for 10 min at 2,000 g and filtrated through a 0.22 μm pore-size filter (Millex G V, Millipore, Molsheim, France). Unbound Dextran is removed by washing in a high-gradient magnetic field (HGMF). HGMF washing of magnetic nanomatrices is performed in steelwool columns made as described below and placed in a magnetic field of approx. 0.6 Tesla (MACS permanent magnet, Miltenyi Biotec GmbH, Bergisch Gladbach, Germany). Ten milliliters of nanomatrix suspension are applied to a 15×40 mm column of 2 g steelwool. The loaded column is washed with 30 ml 0.05 M sodium acetate. After removing the column from the external magnetic field, the magnetic nanomatrices are eluted with 0.05 M sodium acetate. The nanomatrices form a brown suspension. The relative particle concentration is given as optical density at 450 nm. The size of the nanomatrices was determined by electron microscopy and dynamic light scattering to be 30±20 nm (e.m.) and 65±20 nm (DLS). The nanomatrices show superparamagnetic behavior, as determined by susceptibility measurements. The size of the trapped ferrit microcrystals was determined from magnetic measurements to be approximately 10 nm.

CD3 antibodies (clone OKT3) and CD28 antibodies (clone 15E8) (Miltenyi Biotec GmbH, Bergisch Gladbach, Germany) were conjugated to the same or separate nanomatrices by standard bioconjugation chemistry (Bioconjugate Techniques, 2nd Edition, By Greg T. Hermanson, Published by Academic Press, Inc., 2008).

Figure 1:
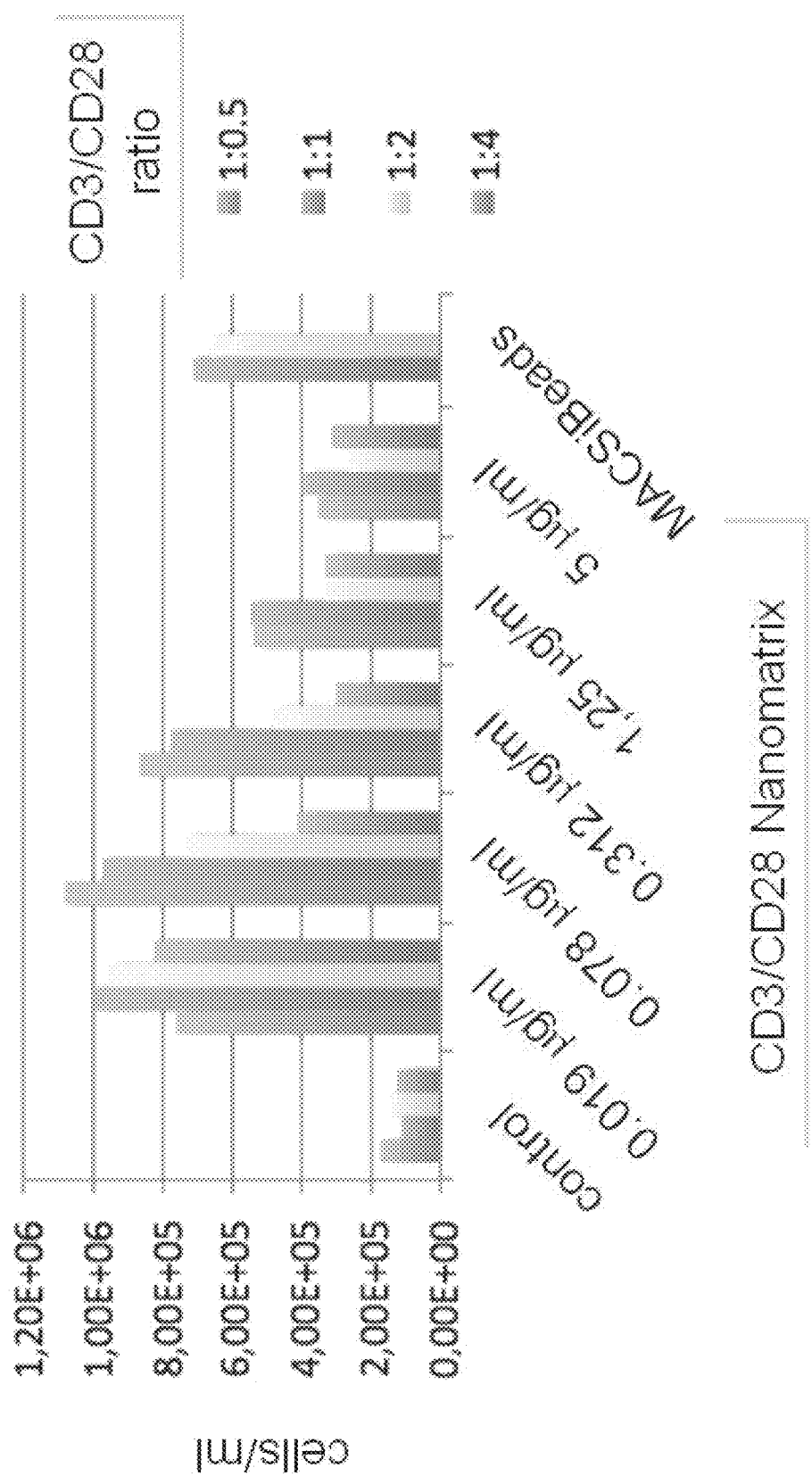
FIG. 1 shows CD3/CD28 Nanomatrices for naive T cell expansion. Sorted human naive CD4 and CD8 T cells were stimulated with CD3/CD28 conjugated nanomatrices at the indicated concentrations (effective CD3 concentration) in the presence of IL-2 for 7 days. Nanomatrices conjugated with CD3 and CD28 in various indicated ratios were compared. As a high control CD3/CD28 conjugated MACSiBeads were used. The absolute number of viable cells in the culture at day 7 is given.

Example 2: Expansion of T Cells Using Nanomatrices at Various CD3/CD28 Concentrations and Ratios Versus CD3/CD28 MACSiBeads The current state-of-the-art reagents for activation of highly purified T cells comprise activating antibodies against CD3/CD28 immobilized either on the surfaces of a cell culture dish or large cell-sized (4-5 μm) particles. Both techniques are error prone and technically difficult to realize and standardize, especially under GMP-compatible production conditions. In contrast nanomatrices can be easily prepared and conveniently be used for cell culture under GMP-conditions. Therefore we compared the T cell activation potential by analysing the expansion potential of the CD3/CD28 coated nanomatrices at various concentrations and CD3/CD28 ratios with commercially available cell stimulation beads (MACSiBeads, ø 4.5 μm, Miltenyi Biotec GmbH). As can be seen in FIG. 1 the nanomatrices expand T cells efficiently even at very low CD3 concentrations (20-100 ng/ml) which are also typically used for soluble CD3/CD28 in the presence of accessory cells which provide crosslinking. Besides the antibody concentration the CD3/CD28 ratio can also influence the cell activation and provides an additional means to optimize the T cell culture. The expansion at optimal doses (20-300 ng/ml) was similar or better than the standard reagent (MACSiBeads). At higher doses the expansion was reduced due to overstimulation of the T cells (activation-induced cell death), a phenomenon known to occur at a too high degree of TCR stimulation. Taken together, these results show that CD3/CD28 coated nanomatrices can efficiently activate and expand T cells at very low antibody concentrations and without the need for additional crosslinking.

Example 3: Comparison CD3/CD28 Conjugated to Nanomatrices Versus 200 nm and 300 nm Solid Particles As outlined above currently available reagents for activation of T cells can be split into two groups. Soluble antibodies stimulating, e.g. against CD3 and CD28, require immobilisation either on a surface of the cell culture dish or via receptors an accessory cells, e.g. Immunoglobulin Fc-receptors. Reagents which do not depend on an extra crosslinking step to be used for T cell activation, e.g. to stimulate highly purified T cells in the absence of accessory cells, are based on cell-sized particles (ø 4-5 μm) coated with stimulating CD3 and CD28 antibodies. It is known that solid particles below a critical diameter of about 1 μm are not suitable to properly expand T cells. To show the unique activating capacity of the CD3/CD28 coated nanomatrices (ø 50-200 nm), we compared their activating capacity with solid particles of similar size (200 nm, and 300 nm) versus cell sized particles (ø 4.5 μm). Since small solid particles do not usually lead to expansion of T cells we analysed early T cell activation markers (CD25 up-regulation and loss of CD3 expression) to have a sensitive screen for T cell activation. CD25 is up-regulated within the first 24-48 hours following T cell stimulation. Because the TCR induced CD25 up-regulation is further supported by IL-2, we also added IL-2 to the culture conditions to maximize the sensitivity of the assay. Another direct result of TCR stimulation is the downregulation of the T cell receptor, which can be analysed via loss of CD3 expression on the cell surface. Highly purified T cells were cultured with CD3/CD28 coated nanomatrices (100 ng/ml CD3) or solid particles with a diameter of 4.5 μm (MACSiBeads) or 200 nm (Ademtech beads) both covalently coated with CD3 and CD28 antibodies. MACSiBeads were used at an optimal 1:1 ratio whereas 200 nm particles were titrated to achieve an active dose of CD3 and CD28 ranging from 25-3000 ng/ml CD3. On day 3 and 5 the frequency of CD25+ T cells and on day 3 the expression intensity of CD3 was measured.

Figure 2A:
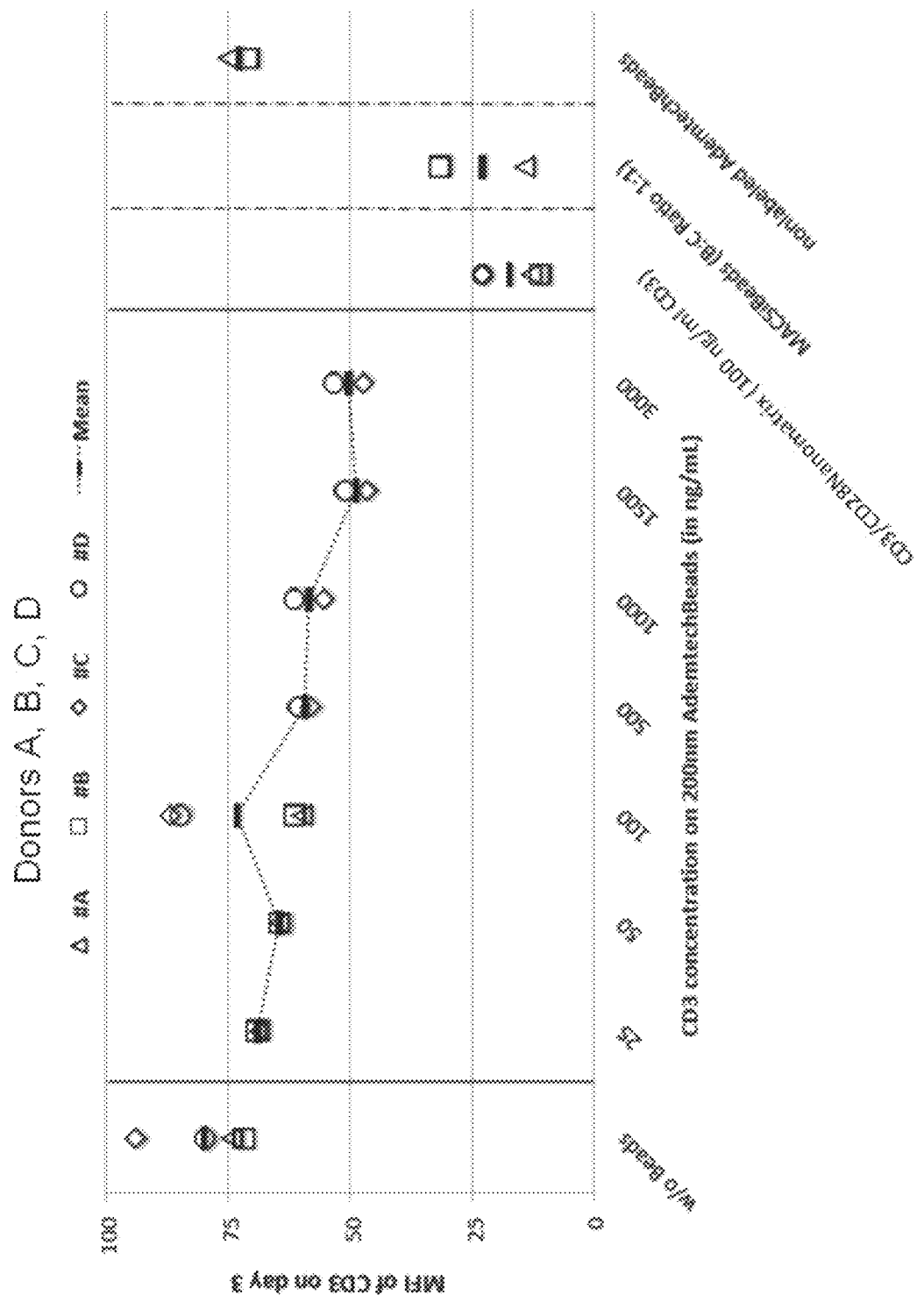
FIGS. 2A, 2B and 2C show nano-sized solid particles versus Nanomatrix for stimulation of T cells. Nano-sized solid particles (AdemtechBeads, diameter=200 nm) were conjugated with CD3/CD28 (1:1) and used for stimulation of naive CD4 and CD8 T cells at the indicated concentrations of CD3. As activation parameters either CD3 down-regulation (FIG. 2A, day 3) or induction of the early activation markers CD25 (day 3 FIG. 2B, day 5 FIG. 2C) were analysed by flow-cytometry. The values were normalized to the value of the same cells stimulated via CD3/CD28 nanomatrix (100 ng/ml CD3). The values from 4 different donors are given.
Figure 2B:
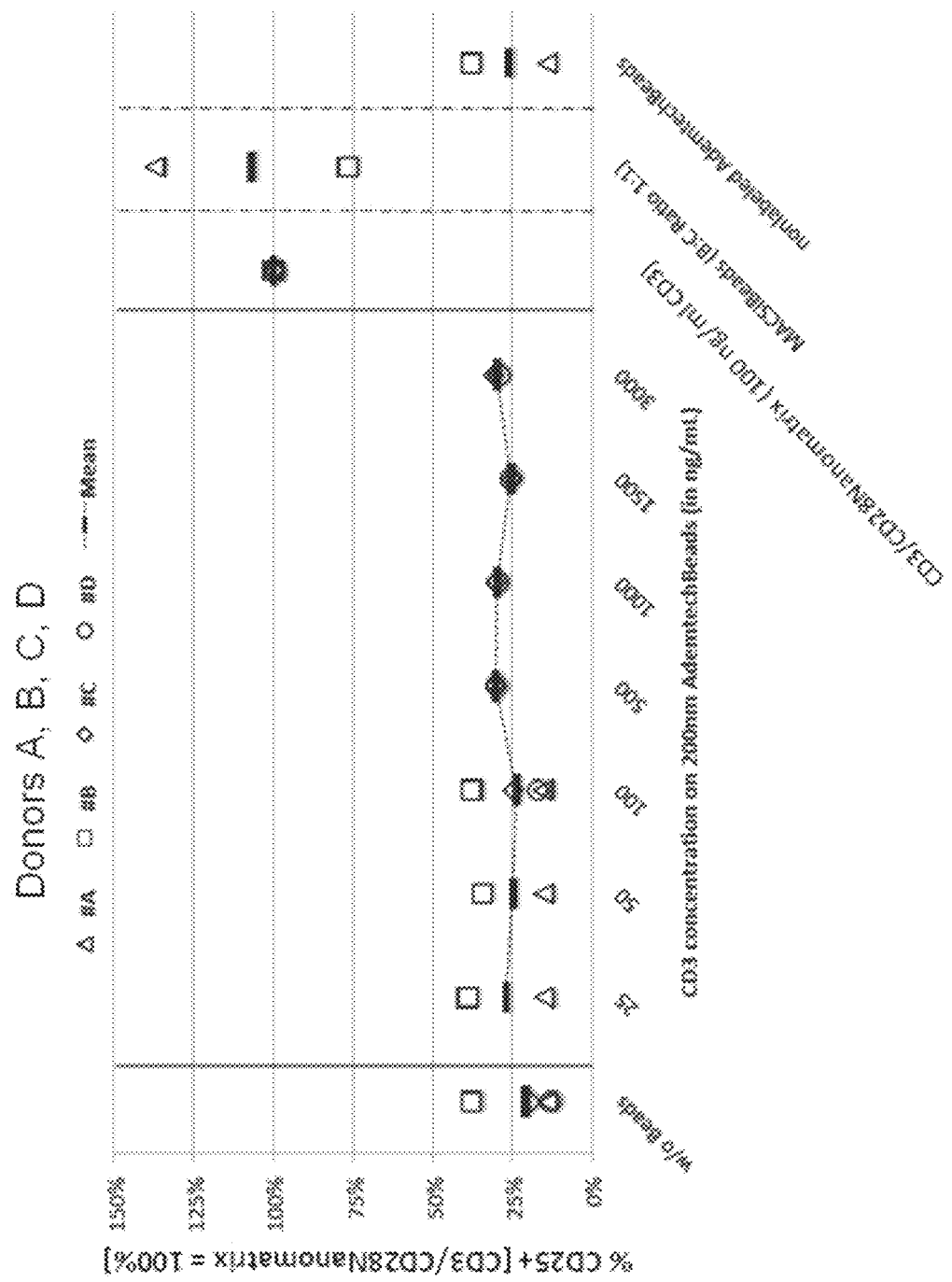
Figure 2C:
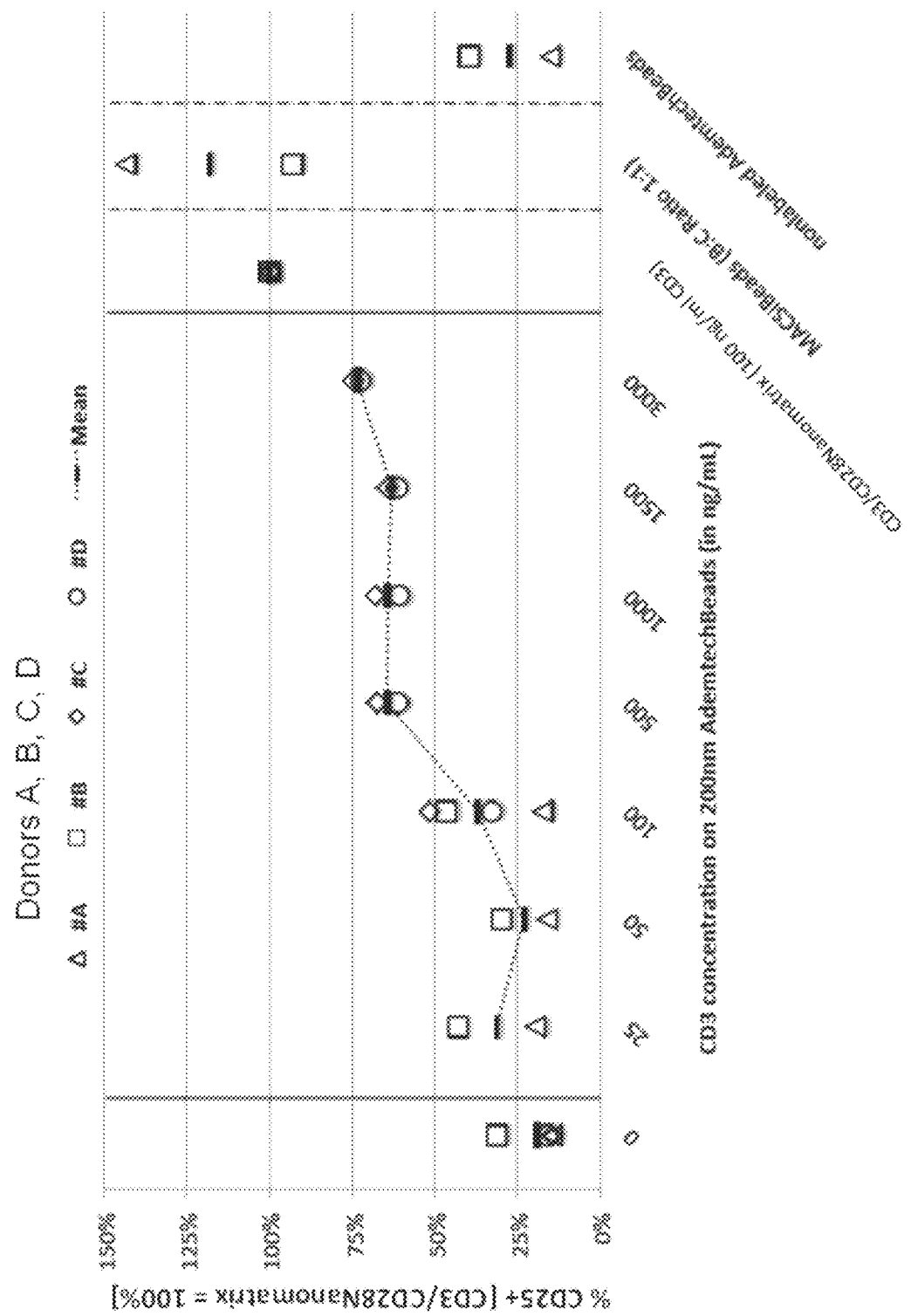

As can be seen in FIGS. 2A, B and C nanomatrices lead to strong activation at the optimal dose (100 ng/ml) as shown by up-regulation of CD25 [FIG. 2B (day 3), FIG. 2C (day 5)] and downregulation of CD3 (FIG. 2A) which occurred at similar levels like with the cell-sized MACSiBeads. In sharp contrast no CD25 up-regulation and almost no CD3 down-regulation was seen for 200 nm solid particles even at 30 fold higher CD3/CD28 concentrations. Even on day five 200 nm solid particles were not able to induce CD25 expression to a similar level like the nanomatrix. Only at high concentrations (5-30 fold higher than for the nanomatrix) there was a slight upregulation observed achieving about 50-70% of the levels of the nanomatrix.

These data show that despite their small size flexible nanomatrices indeed have a unique potential to activate T cells when compared to similarly sized particles with a solid surface. The titration experiment also shows that the lack of activation by CD3/CD28 coated 200-300 nm-sized solid particles cannot simply be compensated by higher doses of particles but obviously there is a different quality of activation signal induced by the nanomatrix.

Example 4: Expansion of Purified T Cell Subsets

Figure 3:
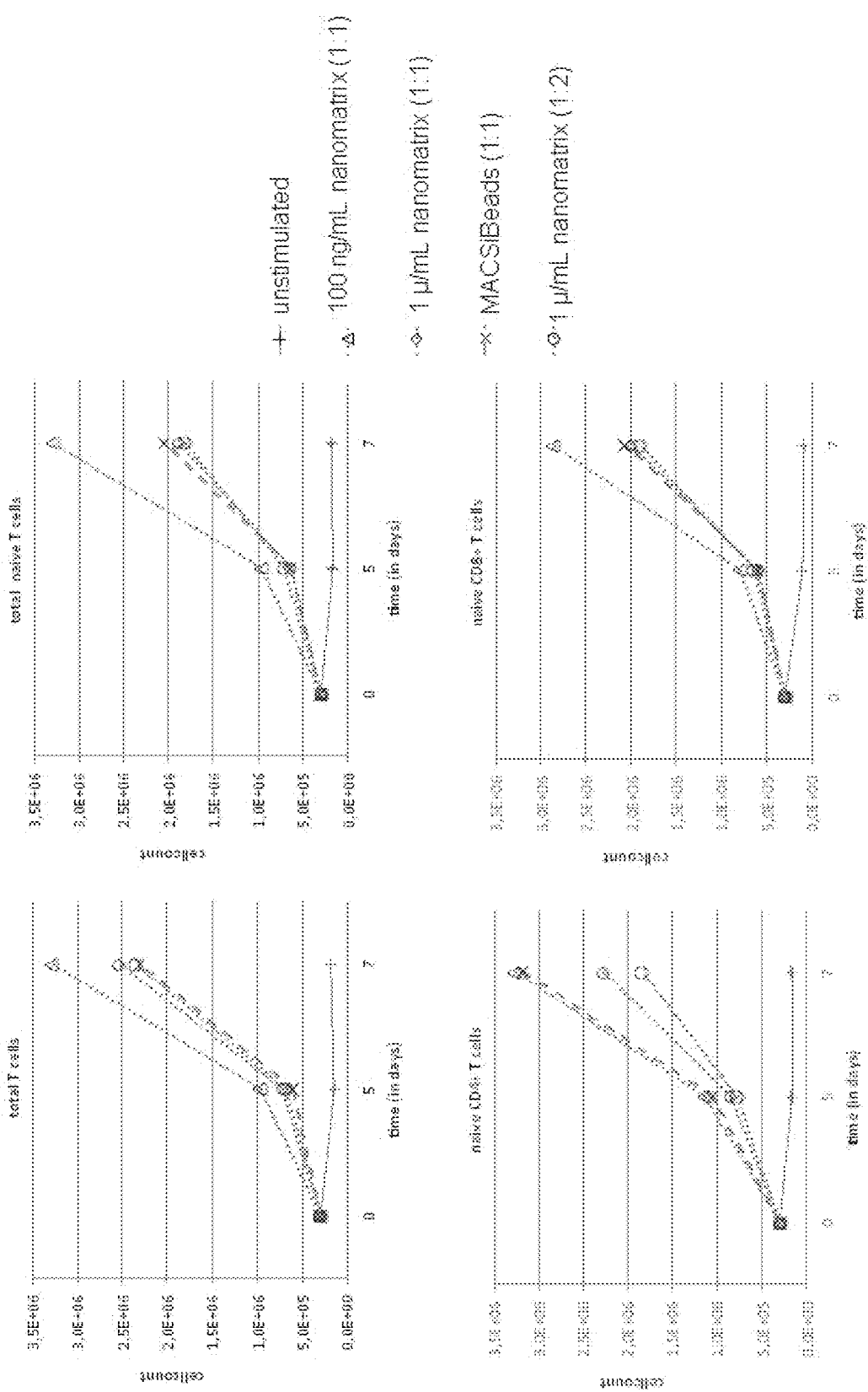
FIG. 3 shows expansion of sorted human T cell populations: Human T cells were sorted into various subpopulations (total T cells, total naive T cells, naive CD4+ T cells, naive CD8+ T cells) and stimulated with CD3/CD28 conjugated nanomatrices at the indicated concentrations (effective CD3 concentration) and a CD3/CD28 ratio of 1:1 in the presence of IL-2 for 7 days. As a high control CD3/CD28 conjugated MACSiBeads were used. The absolute number of viable cells in the culture at day 7 is given.

As indicated above various T cell subsets can have different activation requirements. In particular naïve T cells are difficult to activate in the absence of accessory cells. Furthermore CD4 and CD8 T cells may have different needs when activated alone or in presence of additional cell types. To show that all T cell subsets can be expanded equally well by nanomatrices, we activated purified CD4 and CD8 naïve T cells, total naïve T cells or total T cells with either nanomatrices at the indicated dose and composition or MACSiBeads and compared their expansion. As shown in FIG. 3 all subsets can be efficiently expanded by nanomatrices and at comparable level to the standard MACSiBead culture.

Example 5: Expansion of CD25+Foxp3+ Regulatory T Cells (Treg)

Figure 4:
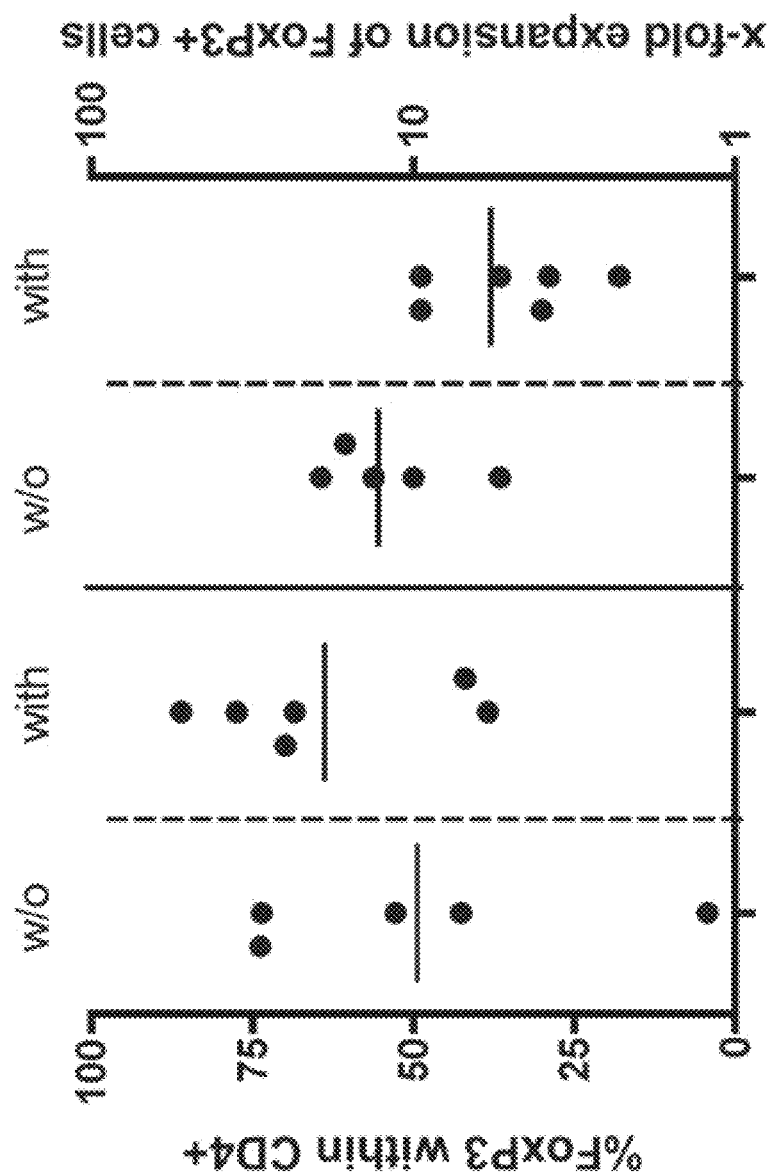
FIG. 4 shows expansion of human Treg: CD25+ Treg were isolated from PBMC by magnetic CD25 selection and expanded in the presence or absence of 100 nM Rapamycin for 14 days using CD3/CD28 nanomatrix (200 ng/ml CD3) and high dose IL-2. On day 7 the cells were restimulated by adding fresh nanomatrix+IL-2. On day 14 the number of viable Treg was determined. The frequency of Foxp3 expressing cells was determined by intracellular immunofluorescence. Each dot represents an individual healthy donor.

Treg are of particular interest for therapeutic applications for transplantation, autoimmunity and chronic inflammation and Treg are difficult to expand in vitro without loss of regulatory activity, i.e. Foxp3 expression. Therefore we also analysed whether CD25 selected Treg cells (Foxp3 purity typically 60-90%) from various donors can be expanded using nanomatrices. To support growth of Treg versus conventional T cells the expansion was done in the presence of 100 nM Rapamycine, a well described drug inhibiting conventional T cell growth. As shown in FIG. 4 following 14 days of culture Treg can be expanded 10-20 times (w/o Rapa) or 5-10 times (with Rapa). As described before without Rapa the Foxp3 purity was highly variable (10-75%) whereas in the presence of Rapa the purity was always >50%.

Taken together these results show that nanomatrices can even be used to activate and expand Treg in culture.

Example 6: Comparison of T Cell Activation by CD3/CD28-Conjugated to the Same Nanomatrix Versus CD3 and CD28 Conjugated to Separate Nanomatrices It is described in various applications of CD3 and CD28 based T cell activation reagents that both antibodies have to be immobilized onto the same surface for optimal activation. Therefore we also tested whether this is also required for CD3 and CD28 conjugated to nanomatrices. We compared expansion of purified naive T cells activated by a CD3/CD28 nanomatrix versus CD3 nanomatrix+CD28 nanomatrix mixed at different ratios/concentrations. Expansion (day 5) and cell division (day 7), as measured by Violetye dilution was analysed. As shown in FIGS. 5A, B the stimulation with the CD3 nanomatrix alone did not induce significant expansion and only few cell divisions can be observed, as it is expected for naive T cells which depend on a costimulatory signal. However addition of the CD28 nanomatrix, already at 10-50 ng/ml induced full cell dividing activity and also expansion of T cell numbers, which was similar to the CD3/CD28 control nanomatrix or the standard MACSiBeads. These data clearly show that both antibodies may be conjugated to separate nanomatrices, which can be mixed hereafter for optimised use. This facilitates the production process and quality control of the single nanomatrices and improves the flexibility of the reagent, e.g. facilitating the optimisation of the activation conditions for specialised T cell subsets by titrating various CD3 and CD28 concentrations and ratios (fine-tuning).

Example 7: The Effect of Conjugation of Soluble CD3 or CD28 to the Nanomatrix

To rule out the possibility that similar results as with the CD3 and/or CD28 coated nanomatrix could be achieved by use of the respective soluble antibodies, we compared the stimulating effects of CD3 or CD28 coated the nanomatrix with soluble antibodies at various concentrations to demonstrate that indeed the conjugation of the antibodies to the matrix is the critical step to obtain good T cell activation. IL-2 was added to all cultures. As shown in FIG. 6A a soluble CD3 alone did not induce any significant up-regulation of the early activation markers CD25 and CD69 in naïve T cells over a wide concentration range (10-10000 ng/ml) whereas CD3 coated Nanomatrix (100 ng/ml CD3) induced CD25/CD69 expression in 20-60% of the cells. In the presence of a saturating amount (200 ng/ml) of soluble CD28 as costimulator (FIG. 6B) soluble CD3 also induced CD25/CD69 expression in about 20-40% of the cells at the highest tested doses (100-10000 ng/ml). In contrast the CD3 coated nanomatrix (100 ng/ml CD3) induced CD25/CD69 expression in 40-70% of the cells.

We also tested the effect of conjugation of CD28 antibodies to the nanomatrix. Since the effects of costimulation are best visualized under suboptimal CD3 stimulation, we titrated CD28 either soluble or conjugated to the nanomatrix in the presence of soluble CD3 to a culture of naïve T cells. As shown in FIG. 6C soluble CD3 alone similar to the induction of CD25/CD69 as shown above did not induce any expansion of the naïve T cells. In the presence of soluble CD28 however a 2-6 fold expansion was detectable but only at the highest tested dose of CD28 (10000 ng/ml). In contrast to this, CD28 conjugated to nanomatrix induced a similar degree of expansion already at a 1000 fold lower concentration (10 ng/ml).

These data show again the strong crosslinking and T cell activating capacity of nanomatrix versus soluble antibodies which explains why CD3CD28 conjugated nanomatrices in contrast to soluble antibodies can be used to activate and expand even naïve human T cells in vitro.

Example 8: Nanomatrices can be Used to Activate T Cells for Introduction of TCR Genes by Viral Transduction One important application for activating and expanding T cells and in particular purified cell subsets is their genetic manipulation, e.g. to introduce a certain antigen receptor with specificity for tumor antigens. We have used nanomatrices to activate purified naïve ($T_N$, CD62L+ CD45RA+), central memory ($T_{CM}$, CD62L+CD45RA−) and effector ($T_{EM}$, CD62L−CD45RA−) T cells and transduced them using a retroviral vector expressing a TCR specific for MART-1, a tumor antigen. To test the relative frequency of transgene expression in these T cell subsets we performed MHC-peptide Class I tetramer staining. All T cell subsets are efficiently transduced (>50%) independent on the stimulatory conditions we tested (FIG. 7). We also compared the in vitro expansion of the transduced T cells. As shown in FIG. 8 after 10 days we observed no differences with regard to expansion of the three subsets under all conditions. All activation regimens for the isolated T cell subsets were equal or better to the "standard" stimulation of total PBMC with soluble CD3 (all values were normalized to this standard to allow better comparison between different donors). We observed a trend (not statistically significant) for better expansion when T cell subsets are stimulated with MACSiBeads or nanomatrices when compared to coated αCD3+ αCD28. We further investigated the functional activity of the introduced MART-1 TCR and the differentiation status of transduced cells looking at surface markers and cytokine production upon re-stimulation with a MART-1+HLA-A2+ tumor cell line. As shown in FIG. 9 nanomatrix- and MACSiBead-stimulated $T_{cm}$ and $T_N$ cells seem to have a higher expression of CD62L and CCR7, two molecules facilitating migration of the T cells into peripheral lymph nodes. This capacity is regarded as beneficial to promote long term persistence and functional activity of transferred T cells in vivo and thus is thought to increase therapeutic efficacy. The percentage of MART-1 reactive IFNγ$^+$ cells tend to be higher in $T_{CM}$ and $T_{EM}$ CD8$^+$ T cell subsets compare to $T_N$ in all stimulatory conditions but this was not statistically significant (FIG. 10 top panel). Focussing on the IL-2 production (FIG. 10 middle panel) we observed that a higher percentage of $T_N$ cells produces IL-2 when they have been stimulated with MACSiBeads/nanomatrices when compared to coated αCD3+αCD28 stimulation. The same is true for TNFα producing cells detected in $T_N$ subset when stimulated with MACSiBeads (FIG. 10 bottom panel). These results indicate cells of $T_N$ derived cells stimulated with beads showed diminished effector cell differentiation, suggesting less progress toward terminal differentiation.

Taken together, the results indicate that CD3/CD28 nanomatrices can be used to efficiently activate and transduce purified T cell subsets to generate fully functional T cell transplants, e.g. for tumor therapy.

The invention claimed is:

1. An in vitro method for polyclonal stimulation of T cells, the method comprising contacting a population of T cells with a nanomatrix, the nanomatrix comprising
    a) a flexible matrix, wherein said matrix is of polymeric dextran material having an average molecular weight of 40,000 daltons; and
    b) attached to said polymeric flexible matrix agents for polyclonal stimulation which provide activation signals to the T cells; thereby activating and inducing the T cells to proliferate, wherein the agents for polyclonal stimulation are anti-CD3 antibodies or antigen binding fragments thereof and anti-CD28 antibodies or antigen binding fragments thereof, wherein the anti-CD3 antibodies or antigen binding fragments thereof and the anti-CD28 antibodies or antigen binding fragments thereof are attached to the same flexible matrix or attached to separate flexible matrices.

2. The method according to claim 1, wherein the nanomatrix is biologically inert with regard to alteration of the cell function.

3. The method according to claim 1 wherein at least one first and one second stimulatory agents are attached to the same flexible matrix.

4. The method according to claim 1 wherein at least one first and one second stimulatory agents are attached to separate flexible matrices.

5. The method according to claim 4, wherein the ratio of nanomatrices to cells is larger than 500:1 allowing fine-tuning of T cell stimulation.

6. The method according to claim 1 wherein the nanomatrix is biodegradable.

7. The method according to claim 1, wherein the nanomatrix carries magnetic, paramagnetic or superparamagnetic nano-crystals, embedded into the flexible matrix.

8. The method according to claim 1, wherein the agent for polyclonal stimulation is attached at high density with more than 25 µg per mg nanomatrix.

9. The method according to claim 1, wherein the stimulated T cells are Treg cells.

10. The method according to claim 1, wherein the method is used within a closed cell culture system.

11. The method according to claim 1, wherein said agents are antigen binding portions of an antibody.

12. The method according to claim 1, wherein said agents are Fabs.

* * * * *